United States Patent
Cragg et al.

(10) Patent No.: US 9,737,426 B2
(45) Date of Patent: Aug. 22, 2017

(54) ENDOGRAFT DEVICE DELIVERY SYSTEMS AND ASSOCIATED METHODS

(71) Applicant: Altura Medical, Inc., Menlo Park, CA (US)

(72) Inventors: Andrew H. Cragg, Edina, MN (US); John Logan, Plymouth, MN (US)

(73) Assignee: Altura Medical, Inc., Menlo Park, CA (US)

( * ) Notice: Subject to any disclaimer, the term of this patent is extended or adjusted under 35 U.S.C. 154(b) by 445 days.

(21) Appl. No.: 14/213,823

(22) Filed: Mar. 14, 2014

(65) Prior Publication Data

US 2014/0277367 A1    Sep. 18, 2014

Related U.S. Application Data

(60) Provisional application No. 61/786,364, filed on Mar. 15, 2013.

(51) Int. Cl.
*A61F 2/966* (2013.01)
*A61F 2/07* (2013.01)
(Continued)

(52) U.S. Cl.
CPC ............. *A61F 2/966* (2013.01); *A61F 2/07* (2013.01); *A61F 2/90* (2013.01); *A61F 2/954* (2013.01);
(Continued)

(58) Field of Classification Search
CPC .. A61F 2/95; A61F 2/954; A61F 2/962; A61F 2/966; A61F 2002/061;
(Continued)

(56) References Cited

U.S. PATENT DOCUMENTS

| 4,562,596 A | 1/1986 | Kornberg |
| 4,655,771 A | 4/1987 | Wallsten |

(Continued)

FOREIGN PATENT DOCUMENTS

| CN | 1248157 A | 3/2000 |
| CN | 1272053 | 11/2000 |

(Continued)

OTHER PUBLICATIONS

U.S. Appl. No. 12/958,367, filed Dec. 1, 2010, Cragg et al.

(Continued)

*Primary Examiner* — Elizabeth Houston
*Assistant Examiner* — Charles Wei
(74) *Attorney, Agent, or Firm* — Craig A. Fieschko, Esq.; DeWitt Ross & Stevens S.C.

(57) ABSTRACT

Modular endograft devices and associated systems and methods are disclosed herein. In several embodiments, an endograft system can include constrained first and second endograft devices that extend across a vascular defect and expanded to press mating septal walls against each other. At least one of the endograft devices can include a fenestration that is aligned with a renal artery to provide bloodflow to the artery. A delivery device configured in accordance with the present technology can include a guidewire that passes through the fenestration to guide the endograft to an implant site and self align the fenestration with the renal artery to facilitate connection of the endograft to the renal artery. An additional stent can be connected to the fenestration to secure the renal artery to the endograft device.

13 Claims, 9 Drawing Sheets

(51) Int. Cl.
*A61F 2/90* (2013.01)
*A61F 2/954* (2013.01)
*A61F 2/06* (2013.01)

(52) U.S. Cl.
CPC ... *A61F 2002/061* (2013.01); *A61F 2002/067* (2013.01); *A61F 2230/0063* (2013.01)

(58) Field of Classification Search
CPC .......... A61F 2002/065; A61F 2002/067; A61F 2250/006; A61B 17/12118; A61M 2025/0681
USPC ................................................ 623/1.11, 1.13
See application file for complete search history.

(56) References Cited

U.S. PATENT DOCUMENTS

| | | |
|---|---|---|
| 4,990,151 A | 2/1991 | Wallsten |
| 5,078,726 A | 1/1992 | Kreamer |
| 5,160,341 A | 11/1992 | Brenneman et al. |
| 5,201,757 A | 4/1993 | Heyn et al. |
| 5,316,023 A | 5/1994 | Palmaz et al. |
| 5,360,443 A | 11/1994 | Barone et al. |
| 5,364,352 A | 11/1994 | Cimino et al. |
| 5,397,345 A | 3/1995 | Lazarus |
| 5,415,664 A | 5/1995 | Pinchuk |
| 5,433,723 A | 7/1995 | Lindenberg et al. |
| 5,445,646 A | 8/1995 | Euteneuer et al. |
| 5,464,449 A | 11/1995 | Ryan et al. |
| 5,476,505 A | 12/1995 | Limon |
| 5,476,506 A | 12/1995 | Lunn |
| 5,480,423 A | 1/1996 | Ravenscroft et al. |
| 5,507,731 A | 4/1996 | Hernandez et al. |
| 5,507,769 A | 4/1996 | Marin et al. |
| 5,522,880 A | 6/1996 | Barone et al. |
| 5,549,552 A * | 8/1996 | Peters ............... A61M 25/1034 604/103.1 |
| 5,562,724 A | 10/1996 | Vorwerk et al. |
| 5,571,170 A | 11/1996 | Palmaz et al. |
| 5,571,171 A | 11/1996 | Barone et al. |
| 5,571,173 A | 11/1996 | Parodi |
| 5,575,818 A | 11/1996 | Pinchuk et al. |
| 5,578,071 A | 11/1996 | Parodi |
| 5,578,072 A | 11/1996 | Barone et al. |
| 5,591,195 A | 1/1997 | Taheri et al. |
| 5,591,228 A | 1/1997 | Edoga |
| 5,591,229 A | 1/1997 | Parodi |
| 5,609,627 A | 3/1997 | Goicoechea et al. |
| 5,626,604 A | 5/1997 | Cottone, Jr. |
| 5,628,783 A * | 5/1997 | Quiachon ................. A61F 2/07 606/194 |
| 5,628,788 A | 5/1997 | Pinchuk |
| 5,632,763 A | 5/1997 | Glastra |
| 5,632,772 A | 5/1997 | Alcime et al. |
| 5,639,278 A | 6/1997 | Dereume et al. |
| 5,653,743 A | 8/1997 | Martin |
| 5,662,606 A | 9/1997 | Cimino et al. |
| 5,683,450 A | 11/1997 | Goicoechea et al. |
| 5,683,453 A | 11/1997 | Palmaz |
| 5,690,644 A * | 11/1997 | Yurek ....................... A61F 2/95 606/198 |
| 5,693,084 A | 12/1997 | Chuter |
| 5,693,087 A | 12/1997 | Parodi |
| 5,707,376 A | 1/1998 | Kavteladze et al. |
| 5,713,917 A | 2/1998 | Leonhardt et al. |
| 5,716,365 A | 2/1998 | Goicoechea et al. |
| 5,749,825 A * | 5/1998 | Fischell .................... A61F 2/90 600/3 |
| 5,755,734 A | 5/1998 | Richter et al. |
| 5,755,735 A | 5/1998 | Richter et al. |
| 5,755,770 A | 5/1998 | Ravenscroft |
| 5,759,186 A | 6/1998 | Bachmann et al. |
| 5,776,142 A | 7/1998 | Gunderson |
| 5,817,102 A | 10/1998 | Johnson et al. |
| 5,824,041 A | 10/1998 | Lenker et al. |
| 5,824,058 A | 10/1998 | Ravenscroft et al. |
| 5,833,694 A | 11/1998 | Poncet |
| 5,843,160 A | 12/1998 | Rhodes |
| 5,855,598 A | 1/1999 | Pinchuk |
| 5,871,536 A | 2/1999 | Lazarus |
| 5,888,201 A | 3/1999 | Stinson et al. |
| 5,897,587 A | 4/1999 | Martakos et al. |
| 5,904,713 A | 5/1999 | Leschinsky |
| 5,906,619 A | 5/1999 | Olson et al. |
| 5,916,263 A | 6/1999 | Goicoechea et al. |
| 5,928,279 A | 7/1999 | Shannon et al. |
| 5,968,068 A | 10/1999 | Dehdashtian et al. |
| 5,984,955 A | 11/1999 | Wisselink |
| 5,984,964 A | 11/1999 | Roberts et al. |
| 5,993,481 A | 11/1999 | Marcade et al. |
| 6,001,125 A | 12/1999 | Golds et al. |
| 6,004,348 A | 12/1999 | Banas et al. |
| 6,015,431 A | 1/2000 | Thornton et al. |
| 6,019,778 A | 2/2000 | Wilson et al. |
| 6,024,763 A | 2/2000 | Lenker et al. |
| 6,039,749 A * | 3/2000 | Marin ...................... A61F 2/07 604/103.07 |
| 6,042,589 A | 3/2000 | Marianne |
| 6,051,020 A | 4/2000 | Goicoechea et al. |
| 6,053,899 A | 4/2000 | Slanda et al. |
| 6,060,128 A | 5/2000 | Kim et al. |
| 6,070,589 A | 6/2000 | Keith et al. |
| 6,077,296 A | 6/2000 | Shokoohi et al. |
| 6,090,128 A | 7/2000 | Douglas |
| 6,090,133 A | 7/2000 | Richter et al. |
| 6,099,558 A | 8/2000 | White et al. |
| 6,102,940 A | 8/2000 | Robichon et al. |
| 6,117,156 A | 9/2000 | Richter et al. |
| 6,117,167 A | 9/2000 | Goicoechea et al. |
| 6,120,522 A | 9/2000 | Vrba et al. |
| 6,126,685 A | 10/2000 | Lenker et al. |
| 6,129,756 A | 10/2000 | Kugler et al. |
| 6,146,415 A | 11/2000 | Fitz |
| 6,156,063 A | 12/2000 | Douglas |
| 6,162,237 A | 12/2000 | Chan |
| 6,162,246 A | 12/2000 | Barone |
| 6,165,195 A * | 12/2000 | Wilson .................... A61F 2/856 606/108 |
| 6,165,213 A | 12/2000 | Goicoechea et al. |
| 6,168,610 B1 | 1/2001 | Marin et al. |
| 6,168,616 B1 | 1/2001 | Brown, III |
| 6,171,277 B1 | 1/2001 | Ponzi |
| 6,174,330 B1 | 1/2001 | Stinson |
| 6,179,809 B1 | 1/2001 | Khairkhahan et al. |
| 6,183,444 B1 | 2/2001 | Glines et al. |
| 6,183,481 B1 | 2/2001 | Lee et al. |
| 6,187,036 B1 | 2/2001 | Shaolian et al. |
| 6,190,360 B1 | 2/2001 | Iancea et al. |
| 6,197,049 B1 | 3/2001 | Shaolian et al. |
| 6,200,339 B1 | 3/2001 | Leschinsky et al. |
| 6,203,550 B1 | 3/2001 | Olson |
| 6,210,422 B1 | 4/2001 | Douglas |
| 6,217,609 B1 | 4/2001 | Haverkost |
| 6,221,090 B1 * | 4/2001 | Wilson .................... A61F 2/856 606/194 |
| 6,221,102 B1 | 4/2001 | Baker et al. |
| 6,230,476 B1 | 5/2001 | Carr et al. |
| 6,231,597 B1 | 5/2001 | Deem et al. |
| 6,238,402 B1 | 5/2001 | Sullivan, III et al. |
| 6,261,316 B1 | 7/2001 | Shaolian et al. |
| 6,267,783 B1 | 7/2001 | Letendre et al. |
| 6,270,525 B1 | 8/2001 | Letendre et al. |
| 6,290,731 B1 | 9/2001 | Solovay et al. |
| 6,302,906 B1 | 10/2001 | Goicoechea et al. |
| 6,306,141 B1 | 10/2001 | Jervis |
| 6,306,164 B1 | 10/2001 | Kujawski |
| 6,306,424 B1 | 10/2001 | Vyakarnam et al. |
| 6,309,413 B1 | 10/2001 | Dereume et al. |
| 6,325,819 B1 | 12/2001 | Pavcnik et al. |
| 6,325,822 B1 | 12/2001 | Chouinard et al. |
| 6,325,826 B1 * | 12/2001 | Vardi ....................... A61F 2/82 623/1.15 |
| 6,331,190 B1 | 12/2001 | Shokoohi et al. |
| 6,331,191 B1 | 12/2001 | Chobotov |

(56) References Cited

U.S. PATENT DOCUMENTS

| | | | |
|---|---|---|---|
| 6,344,052 B1 | 2/2002 | Greenan et al. | |
| 6,344,056 B1 | 2/2002 | Dehdashtian | |
| 6,371,963 B1 | 4/2002 | Nishtala et al. | |
| 6,383,193 B1 | 5/2002 | Cathcart et al. | |
| 6,387,120 B2* | 5/2002 | Wilson | A61F 2/856 623/1.11 |
| 6,391,033 B2 | 5/2002 | Ryan | |
| 6,391,051 B2 | 5/2002 | Sullivan, III et al. | |
| 6,395,019 B2 | 5/2002 | Chobotov | |
| 6,398,802 B1 | 6/2002 | Yee | |
| 6,398,807 B1 | 6/2002 | Chouinard et al. | |
| 6,409,750 B1 | 6/2002 | Hyodoh et al. | |
| 6,413,269 B1 | 7/2002 | Bui et al. | |
| 6,416,542 B1 | 7/2002 | Marcade et al. | |
| 6,440,161 B1* | 8/2002 | Madrid | A61F 2/90 606/108 |
| 6,468,260 B1 | 10/2002 | Bumbalough et al. | |
| 6,478,813 B1 | 11/2002 | Keith et al. | |
| 6,482,227 B1 | 11/2002 | Solovay | |
| 6,488,700 B2 | 12/2002 | Klumb et al. | |
| 6,500,203 B1 | 12/2002 | Thompson et al. | |
| 6,514,261 B1 | 2/2003 | Randall et al. | |
| 6,517,571 B1 | 2/2003 | Brauker et al. | |
| 6,517,572 B2 | 2/2003 | Kugler et al. | |
| 6,517,574 B1 | 2/2003 | Chuter | |
| 6,520,983 B1 | 2/2003 | Colgan et al. | |
| 6,524,336 B1 | 2/2003 | Papazolgou et al. | |
| 6,533,811 B1 | 3/2003 | Ryan et al. | |
| 6,554,794 B1 | 4/2003 | Mueller et al. | |
| 6,554,858 B2 | 4/2003 | Dereume et al. | |
| RE38,146 E | 6/2003 | Palmaz et al. | |
| 6,572,643 B1 | 6/2003 | Gharibadeh | |
| 6,576,006 B2 | 6/2003 | Limon et al. | |
| 6,585,756 B1 | 7/2003 | Strecker | |
| 6,599,315 B2* | 7/2003 | Wilson | A61F 2/856 606/108 |
| 6,602,225 B2 | 8/2003 | Eidenschink et al. | |
| 6,602,280 B2 | 8/2003 | Chobotov | |
| 6,629,981 B2 | 10/2003 | Bui et al. | |
| 6,645,242 B1 | 11/2003 | Quinn | |
| 6,652,567 B1 | 11/2003 | Deaton | |
| 6,656,215 B1 | 12/2003 | Yanez et al. | |
| 6,660,030 B2 | 12/2003 | Shaolian et al. | |
| 6,663,645 B2 | 12/2003 | Nishtala et al. | |
| 6,669,716 B1 | 12/2003 | Gilson et al. | |
| 6,682,557 B1 | 1/2004 | Quiachon et al. | |
| 6,695,875 B2 | 2/2004 | Stelter et al. | |
| 6,730,119 B1 | 5/2004 | Smalling | |
| 6,733,521 B2 | 5/2004 | Chobotov et al. | |
| 6,743,247 B1 | 6/2004 | Levinson et al. | |
| 6,755,854 B2 | 6/2004 | Gillick et al. | |
| 6,761,733 B2 | 7/2004 | Chobotov et al. | |
| 6,773,454 B2 | 8/2004 | Wholey et al. | |
| 6,773,457 B2 | 8/2004 | Ivancev et al. | |
| 6,786,920 B2 | 9/2004 | Shannon et al. | |
| 6,790,225 B1 | 9/2004 | Shannon et al. | |
| 6,792,979 B2 | 9/2004 | Konya et al. | |
| 6,808,529 B2 | 10/2004 | Fulkerson | |
| 6,808,533 B1 | 10/2004 | Goodwin et al. | |
| 6,808,534 B1 | 10/2004 | Escano | |
| 6,814,752 B1 | 11/2004 | Chuter | |
| 6,814,753 B2 | 11/2004 | Schmitt | |
| 6,830,575 B2 | 12/2004 | Stenzel et al. | |
| 6,843,802 B1 | 1/2005 | Villalobos et al. | |
| 6,843,803 B2 | 1/2005 | Ryan et al. | |
| 6,849,084 B2 | 2/2005 | Rabkin et al. | |
| 6,858,038 B2 | 2/2005 | Heuser | |
| 6,866,669 B2 | 3/2005 | Buzzard et al. | |
| 6,878,164 B2 | 4/2005 | Kujawski et al. | |
| 6,887,268 B2 | 5/2005 | Butaric et al. | |
| 6,911,039 B2 | 6/2005 | Shiu et al. | |
| 6,913,594 B2 | 7/2005 | Coleman et al. | |
| 6,926,724 B1 | 8/2005 | Chu | |
| 6,929,661 B2 | 8/2005 | Bolduc et al. | |
| 6,939,352 B2 | 9/2005 | Buzzard et al. | |
| 6,939,371 B2 | 9/2005 | Kugler et al. | |
| 6,942,691 B1 | 9/2005 | Chuter | |
| 6,942,692 B2 | 9/2005 | Landau et al. | |
| 6,951,572 B1 | 10/2005 | Douglas | |
| 6,964,679 B1 | 11/2005 | Marcade et al. | |
| 6,974,471 B2 | 12/2005 | Van Schie et al. | |
| 6,981,982 B2 | 1/2006 | Armstrong et al. | |
| 6,984,243 B2 | 1/2006 | Dwyer et al. | |
| 6,984,244 B2 | 1/2006 | Perez et al. | |
| 7,000,649 B2 | 2/2006 | Takahashi et al. | |
| 7,001,423 B2 | 2/2006 | Euteneuer et al. | |
| 7,014,653 B2 | 3/2006 | Ouriel et al. | |
| 7,018,401 B1 | 3/2006 | Hyodoh et al. | |
| 7,048,014 B2 | 5/2006 | Hyodoh et al. | |
| 7,052,511 B2 | 5/2006 | Weldon et al. | |
| 7,052,513 B2 | 5/2006 | Thompson | |
| 7,063,721 B2 | 6/2006 | Takahashi et al. | |
| 7,074,236 B2 | 7/2006 | Rabkin et al. | |
| 7,105,016 B2 | 9/2006 | Shiu et al. | |
| 7,112,217 B1 | 9/2006 | Kugler et al. | |
| 7,118,592 B1 | 10/2006 | Dang et al. | |
| 7,122,050 B2 | 10/2006 | Randall et al. | |
| 7,122,052 B2 | 10/2006 | Greenhalgh | |
| 7,128,758 B2* | 10/2006 | Cox | A61F 2/86 148/563 |
| 7,131,991 B2 | 11/2006 | Zarins et al. | |
| 7,144,421 B2 | 12/2006 | Carpenter et al. | |
| 7,147,656 B2 | 12/2006 | Andreas et al. | |
| 7,160,318 B2 | 1/2007 | Greenberg et al. | |
| 7,169,118 B2 | 1/2007 | Reynolds et al. | |
| 7,175,651 B2 | 2/2007 | Kerr | |
| 7,220,274 B1 | 5/2007 | Quinn | |
| 7,226,474 B2 | 6/2007 | Iancea et al. | |
| 7,229,472 B2 | 6/2007 | DePalma et al. | |
| 7,232,459 B2 | 6/2007 | Greenberg et al. | |
| 7,238,197 B2 | 7/2007 | Sequin et al. | |
| 7,264,631 B2 | 9/2007 | DiCarlo | |
| 7,264,632 B2 | 9/2007 | Wright et al. | |
| 7,267,685 B2 | 9/2007 | Butaric et al. | |
| 7,278,998 B2 | 10/2007 | Gaschino et al. | |
| 7,294,147 B2* | 11/2007 | Hartley | A61F 2/07 623/1.13 |
| 7,306,623 B2 | 12/2007 | Watson | |
| 7,314,483 B2 | 1/2008 | Landau et al. | |
| 7,314,484 B2 | 1/2008 | Deem et al. | |
| 7,318,835 B2 | 1/2008 | Berra | |
| 7,326,237 B2 | 2/2008 | DePalma et al. | |
| 7,344,557 B2* | 3/2008 | Yadin | A61F 2/856 604/103.06 |
| 7,344,562 B2 | 3/2008 | Feller et al. | |
| 7,357,812 B2 | 4/2008 | Andreas et al. | |
| 7,371,255 B2 | 5/2008 | Richter et al. | |
| RE40,404 E | 6/2008 | Schmitt et al. | |
| 7,402,163 B2 | 7/2008 | Nishtala et al. | |
| 7,435,253 B1* | 10/2008 | Hartley | A61F 2/07 623/1.11 |
| 7,476,244 B2 | 1/2009 | Buzzard et al. | |
| 7,481,836 B2 | 1/2009 | Greenan | |
| 7,488,344 B2 | 2/2009 | Hartley et al. | |
| 7,517,361 B1 | 4/2009 | Ravenscroft | |
| RE40,816 E | 6/2009 | Taylor et al. | |
| 7,550,004 B2 | 6/2009 | Bahler et al. | |
| 7,575,591 B2 | 8/2009 | Howat et al. | |
| 7,588,596 B2 | 9/2009 | Spiridigliozzi et al. | |
| 7,591,846 B2* | 9/2009 | Vardi | A61F 2/856 623/1.35 |
| 7,615,044 B2 | 11/2009 | Scheibe et al. | |
| 7,615,071 B2 | 11/2009 | Chobotov | |
| 7,637,932 B2 | 12/2009 | Bolduc et al. | |
| 7,655,034 B2 | 2/2010 | Mitchell et al. | |
| 7,655,040 B2 | 2/2010 | Douk et al. | |
| 7,666,220 B2 | 2/2010 | Evans et al. | |
| 7,674,282 B2 | 3/2010 | Wu et al. | |
| 7,678,141 B2 | 3/2010 | Greenan et al. | |
| 7,682,381 B2 | 3/2010 | Rakos et al. | |
| 7,691,109 B2 | 4/2010 | Armstrong et al. | |
| 7,691,138 B2 | 4/2010 | Stenzel et al. | |
| 7,695,506 B2 | 4/2010 | Thistle et al. | |
| 7,708,771 B2 | 5/2010 | Chuter et al. | |

(56) References Cited

U.S. PATENT DOCUMENTS

| | | | |
|---|---|---|---|
| 7,758,634 B2* | 7/2010 | Brucker | A61F 2/856 623/1.35 |
| 7,766,960 B2 | 8/2010 | Alexander et al. | |
| 7,766,961 B2 | 8/2010 | Patel et al. | |
| 7,780,717 B2 | 8/2010 | Ducke et al. | |
| 7,828,833 B2 | 11/2010 | Haverkost et al. | |
| 7,828,838 B2 | 11/2010 | Bolduc et al. | |
| 7,837,724 B2 | 11/2010 | Keeble et al. | |
| 7,862,609 B2 | 1/2011 | Butaric et al. | |
| 7,887,576 B2 | 2/2011 | Bahler et al. | |
| 7,918,880 B2 | 4/2011 | Austin | |
| 7,922,740 B2* | 4/2011 | Eidenschink | A61F 2/954 606/194 |
| 7,935,140 B2 | 5/2011 | Griffin | |
| 7,938,852 B2 | 5/2011 | Andreas et al. | |
| 7,993,384 B2 | 8/2011 | Wu et al. | |
| 8,021,410 B2 | 9/2011 | Melsheimer | |
| 8,025,692 B2 | 9/2011 | Feeser | |
| 8,029,555 B2* | 10/2011 | Howell | A61F 2/95 623/1.11 |
| 8,075,606 B2 | 12/2011 | Dorn | |
| 8,080,050 B2 | 12/2011 | Chiang et al. | |
| 8,114,147 B2 | 2/2012 | Wood et al. | |
| 8,136,004 B2 | 3/2012 | Umesh et al. | |
| 8,163,004 B2 | 4/2012 | Amplatz et al. | |
| 8,163,006 B2 | 4/2012 | Feller et al. | |
| 8,164,892 B2 | 4/2012 | An | |
| 8,167,892 B2 | 5/2012 | Feller, III et al. | |
| 8,187,291 B2 | 5/2012 | Nishtala et al. | |
| 8,241,344 B2 | 8/2012 | Kusleika et al. | |
| 8,287,583 B2 | 10/2012 | LaDuca et al. | |
| 8,323,239 B2 | 12/2012 | Bednarek et al. | |
| 8,357,190 B2 | 1/2013 | Fearn et al. | |
| 8,372,131 B2 | 2/2013 | Hestad et al. | |
| 8,377,108 B2* | 2/2013 | Jennings | A61F 2/856 623/1.11 |
| 8,434,393 B2 | 5/2013 | Adams | |
| 8,460,358 B2* | 6/2013 | Andreas | A61F 2/958 623/1.11 |
| 8,470,015 B2 | 6/2013 | Barthold | |
| 8,486,128 B2 | 7/2013 | Jen et al. | |
| 8,858,613 B2 | 10/2014 | Cragg et al. | |
| 2001/0003161 A1* | 6/2001 | Vardi | A61F 2/954 623/1.11 |
| 2001/0014823 A1 | 8/2001 | Ressemann et al. | |
| 2001/0049548 A1* | 12/2001 | Vardi | A61F 2/954 623/1.11 |
| 2002/0013620 A1 | 1/2002 | Kujawski | |
| 2002/0019659 A1 | 2/2002 | Goicoechea et al. | |
| 2002/0019664 A1 | 2/2002 | Douglas | |
| 2002/0058987 A1 | 5/2002 | Butaric et al. | |
| 2002/0143387 A1 | 10/2002 | Soetikno et al. | |
| 2002/0151933 A1 | 10/2002 | Sheldon | |
| 2002/0169497 A1 | 11/2002 | Wholey et al. | |
| 2003/0014075 A1 | 1/2003 | Rosenbluth et al. | |
| 2003/0130720 A1 | 7/2003 | DePalma et al. | |
| 2003/0130725 A1 | 7/2003 | DePalma et al. | |
| 2003/0191516 A1 | 10/2003 | Weldon et al. | |
| 2003/0199967 A1* | 10/2003 | Hartley | A61F 2/07 623/1.13 |
| 2003/0199973 A1 | 10/2003 | Chuter et al. | |
| 2004/0019375 A1 | 1/2004 | Casey et al. | |
| 2004/0054397 A1 | 3/2004 | Smith et al. | |
| 2004/0059406 A1 | 3/2004 | Cully et al. | |
| 2004/0059407 A1 | 3/2004 | Escamilla et al. | |
| 2004/0073288 A1 | 4/2004 | Kerr | |
| 2004/0082989 A1 | 4/2004 | Cook et al. | |
| 2004/0098092 A1 | 5/2004 | Butaric et al. | |
| 2004/0117003 A1 | 6/2004 | Ouriel et al. | |
| 2004/0138734 A1 | 7/2004 | Chobotov et al. | |
| 2004/0143316 A1 | 7/2004 | Spiridigliozzi et al. | |
| 2004/0162604 A1 | 8/2004 | Sowinski et al. | |
| 2004/0167599 A1 | 8/2004 | Goicoechea et al. | |
| 2004/0193245 A1 | 9/2004 | Deem et al. | |
| 2004/0193252 A1 | 9/2004 | Perez et al. | |
| 2004/0215316 A1 | 10/2004 | Smalling | |
| 2004/0230289 A1 | 11/2004 | DiMatteo et al. | |
| 2004/0236406 A1 | 11/2004 | Gregorich | |
| 2004/0260382 A1 | 12/2004 | Fogarty et al. | |
| 2005/0021123 A1 | 1/2005 | Dorn et al. | |
| 2005/0033400 A1 | 2/2005 | Chuter | |
| 2005/0033416 A1 | 2/2005 | Seguin et al. | |
| 2005/0043780 A1 | 2/2005 | Gifford et al. | |
| 2005/0049607 A1 | 3/2005 | Hart et al. | |
| 2005/0085894 A1 | 4/2005 | Kershner | |
| 2005/0113906 A9 | 5/2005 | Bolduc et al. | |
| 2005/0119721 A1 | 6/2005 | Rabkin et al. | |
| 2005/0131516 A1 | 6/2005 | Greenhalgh | |
| 2005/0137677 A1 | 6/2005 | Rush | |
| 2005/0143804 A1 | 6/2005 | Haverkost | |
| 2005/0154441 A1 | 7/2005 | Schaeffer et al. | |
| 2005/0171478 A1* | 8/2005 | Selmon | A61B 17/3207 604/164.01 |
| 2005/0171598 A1 | 8/2005 | Schaeffer | |
| 2005/0222668 A1 | 10/2005 | Schaeffer et al. | |
| 2005/0228475 A1 | 10/2005 | Keeble et al. | |
| 2005/0228484 A1 | 10/2005 | Stephens et al. | |
| 2005/0240258 A1 | 10/2005 | Bolduc et al. | |
| 2005/0273154 A1 | 12/2005 | Colone | |
| 2005/0288772 A1 | 12/2005 | Douglas | |
| 2006/0030921 A1 | 2/2006 | Chu | |
| 2006/0058864 A1 | 3/2006 | Schaeffer et al. | |
| 2006/0069323 A1 | 3/2006 | Elkins et al. | |
| 2006/0074481 A1 | 4/2006 | Vardi et al. | |
| 2006/0085057 A1 | 4/2006 | George et al. | |
| 2006/0095116 A1 | 5/2006 | Bolduc et al. | |
| 2006/0142694 A1 | 6/2006 | Bednarek et al. | |
| 2006/0155359 A1 | 7/2006 | Watson | |
| 2006/0155366 A1 | 7/2006 | LaDuca et al. | |
| 2006/0161244 A1 | 7/2006 | Seguin | |
| 2006/0178733 A1 | 8/2006 | Pinchuk et al. | |
| 2006/0212112 A1 | 9/2006 | Evans et al. | |
| 2006/0224232 A1* | 10/2006 | Chobotov | A61F 2/07 623/1.16 |
| 2006/0233990 A1 | 10/2006 | Humphrey et al. | |
| 2006/0265055 A1 | 11/2006 | Lauterjung | |
| 2006/0282155 A1 | 12/2006 | Fearn et al. | |
| 2007/0032852 A1 | 2/2007 | Machek et al. | |
| 2007/0051377 A1 | 3/2007 | Douk et al. | |
| 2007/0055341 A1 | 3/2007 | Edoga et al. | |
| 2007/0055360 A1 | 3/2007 | Hanson et al. | |
| 2007/0055363 A1 | 3/2007 | Chuter et al. | |
| 2007/0100429 A1 | 5/2007 | Wu et al. | |
| 2007/0118208 A1 | 5/2007 | Kerr | |
| 2007/0142895 A1 | 6/2007 | Castaneda et al. | |
| 2007/0142896 A1 | 6/2007 | Anderson et al. | |
| 2007/0150041 A1 | 6/2007 | Evans et al. | |
| 2007/0156224 A1 | 7/2007 | Cioanta et al. | |
| 2007/0156229 A1 | 7/2007 | Park | |
| 2007/0162109 A1 | 7/2007 | Davila et al. | |
| 2007/0168017 A1 | 7/2007 | Sarac | |
| 2007/0168018 A1 | 7/2007 | Amplatz et al. | |
| 2007/0173929 A1 | 7/2007 | Boucher et al. | |
| 2007/0179592 A1 | 8/2007 | Schaeffer | |
| 2007/0179600 A1 | 8/2007 | Vardi | |
| 2007/0198077 A1 | 8/2007 | Cully et al. | |
| 2007/0198079 A1 | 8/2007 | Casey et al. | |
| 2007/0219620 A1 | 9/2007 | Eells et al. | |
| 2007/0225797 A1 | 9/2007 | Krivoruhko | |
| 2007/0233220 A1 | 10/2007 | Greenan | |
| 2007/0233222 A1 | 10/2007 | Roeder et al. | |
| 2007/0244542 A1 | 10/2007 | Greenan et al. | |
| 2007/0244547 A1 | 10/2007 | Greenan | |
| 2007/0265697 A1 | 11/2007 | Goicoechea et al. | |
| 2007/0293940 A1 | 12/2007 | Schaeffer et al. | |
| 2008/0015682 A1 | 1/2008 | Majercak et al. | |
| 2008/0046065 A1* | 2/2008 | Hartley | A61F 2/07 623/1.13 |
| 2008/0082154 A1 | 4/2008 | Tseng et al. | |
| 2008/0082158 A1 | 4/2008 | Tseng et al. | |
| 2008/0082159 A1 | 4/2008 | Tseng et al. | |
| 2008/0097572 A1 | 4/2008 | Sheldon et al. | |
| 2008/0108969 A1 | 5/2008 | Kerr | |

(56) References Cited

U.S. PATENT DOCUMENTS

| | | | |
|---|---|---|---|
| 2008/0114435 A1* | 5/2008 | Bowe | A61F 2/95 623/1.11 |
| 2008/0114444 A1 | 5/2008 | Yu | |
| 2008/0114449 A1 | 5/2008 | Gregorich et al. | |
| 2008/0125847 A1 | 5/2008 | Krever et al. | |
| 2008/0132993 A1 | 6/2008 | Rasmussen et al. | |
| 2008/0167704 A1 | 7/2008 | Wright et al. | |
| 2008/0183272 A1 | 7/2008 | Wood et al. | |
| 2008/0195191 A1 | 8/2008 | Luo et al. | |
| 2008/0208325 A1 | 8/2008 | Helmus et al. | |
| 2008/0221659 A1 | 9/2008 | Hartley et al. | |
| 2008/0221668 A1 | 9/2008 | Pinchuk et al. | |
| 2008/0249601 A1 | 10/2008 | Kerr | |
| 2008/0262595 A1* | 10/2008 | Chu | A61F 2/064 623/1.13 |
| 2008/0290076 A1 | 11/2008 | Sheldon et al. | |
| 2009/0030501 A1 | 1/2009 | Morris et al. | |
| 2009/0036973 A1 | 2/2009 | Humphrey et al. | |
| 2009/0043376 A1 | 2/2009 | Hamer et al. | |
| 2009/0085186 A1 | 4/2009 | Meyer | |
| 2009/0099647 A1 | 4/2009 | Glimsdale et al. | |
| 2009/0099649 A1 | 4/2009 | Chobotov et al. | |
| 2009/0105640 A1 | 4/2009 | Bednarek et al. | |
| 2009/0125095 A1 | 5/2009 | Bui et al. | |
| 2009/0138067 A1 | 5/2009 | Pinchuk et al. | |
| 2009/0164001 A1 | 6/2009 | Biggs et al. | |
| 2009/0171451 A1 | 7/2009 | Kuppurathanam et al. | |
| 2009/0173439 A1 | 7/2009 | Hayashi et al. | |
| 2009/0177265 A1 | 7/2009 | Dierking et al. | |
| 2009/0182413 A1 | 7/2009 | Burkart et al. | |
| 2009/0187240 A1 | 7/2009 | Clerc et al. | |
| 2009/0198267 A1 | 8/2009 | Evans et al. | |
| 2009/0228020 A1 | 9/2009 | Wallace et al. | |
| 2009/0248144 A1 | 10/2009 | Bahler et al. | |
| 2009/0264992 A1 | 10/2009 | Fleming, III et al. | |
| 2009/0276035 A1 | 11/2009 | Waysbeyn et al. | |
| 2009/0287145 A1 | 11/2009 | Cragg et al. | |
| 2009/0318949 A1 | 12/2009 | Ganpath et al. | |
| 2009/0319029 A1 | 12/2009 | Evans et al. | |
| 2010/0004728 A1 | 1/2010 | Rao et al. | |
| 2010/0030255 A1 | 2/2010 | Berra et al. | |
| 2010/0030321 A1 | 2/2010 | Mach | |
| 2010/0036360 A1 | 2/2010 | Herbowy et al. | |
| 2010/0049291 A1 | 2/2010 | Yampolsky et al. | |
| 2010/0094394 A1 | 4/2010 | Beach et al. | |
| 2010/0094400 A1 | 4/2010 | Bolduc et al. | |
| 2010/0094403 A1 | 4/2010 | Heraty et al. | |
| 2010/0100167 A1 | 4/2010 | Bortlein et al. | |
| 2010/0106239 A1 | 4/2010 | Roeder | |
| 2010/0262216 A1 | 10/2010 | Xue | |
| 2010/0268327 A1 | 10/2010 | Bruszewski et al. | |
| 2010/0286756 A1 | 11/2010 | Dorn et al. | |
| 2010/0292771 A1 | 11/2010 | Paskar | |
| 2010/0305686 A1 | 12/2010 | Cragg et al. | |
| 2011/0022149 A1 | 1/2011 | Cox et al. | |
| 2011/0079315 A1 | 4/2011 | Norton et al. | |
| 2011/0125248 A1 | 5/2011 | George et al. | |
| 2011/0130819 A1 | 6/2011 | Cragg et al. | |
| 2011/0130820 A1* | 6/2011 | Cragg | A61F 2/07 623/1.11 |
| 2011/0130824 A1 | 6/2011 | Cragg et al. | |
| 2011/0130825 A1 | 6/2011 | Cragg et al. | |
| 2011/0130826 A1 | 6/2011 | Cragg et al. | |
| 2011/0178589 A1 | 7/2011 | Andreas et al. | |
| 2011/0213450 A1 | 9/2011 | Maclean et al. | |
| 2011/0257673 A1 | 10/2011 | Heraty et al. | |
| 2011/0257720 A1 | 10/2011 | Peterson et al. | |
| 2011/0264074 A1 | 10/2011 | Tegg et al. | |
| 2011/0295354 A1 | 12/2011 | Bueche et al. | |
| 2011/0313505 A1 | 12/2011 | McHugo | |
| 2012/0041536 A1 | 2/2012 | Hansen | |
| 2012/0130469 A1 | 5/2012 | Cragg et al. | |
| 2012/0158115 A9 | 6/2012 | Arnault De La Menardiere et al. | |
| 2012/0158117 A1 | 6/2012 | Ryan | |
| 2012/0165919 A1 | 6/2012 | Cox et al. | |
| 2012/0172968 A1 | 7/2012 | Chuter et al. | |
| 2012/0185031 A1 | 7/2012 | Ryan et al. | |
| 2012/0197376 A1 | 8/2012 | Heidner et al. | |
| 2012/0209063 A1 | 8/2012 | Nishtala et al. | |
| 2012/0221091 A1 | 8/2012 | Hartly et al. | |
| 2012/0221093 A1 | 8/2012 | McHugo | |
| 2012/0330398 A1 | 12/2012 | Hyodoh et al. | |
| 2013/0035749 A1 | 2/2013 | Farag | |
| 2013/0096407 A1 | 4/2013 | Bednarek et al. | |
| 2013/0123898 A1 | 5/2013 | Tung et al. | |
| 2013/0131774 A1 | 5/2013 | Nabulsi et al. | |
| 2013/0211505 A1* | 8/2013 | Robison | A61F 2/07 623/1.35 |
| 2014/0046428 A1 | 2/2014 | Cragg et al. | |
| 2014/0046429 A1 | 2/2014 | Cragg et al. | |
| 2014/0052232 A1 | 2/2014 | Cragg et al. | |

FOREIGN PATENT DOCUMENTS

| | | |
|---|---|---|
| EP | 808613 | 11/1997 |
| EP | 971646 | 9/2004 |
| EP | 1803418 | 7/2007 |
| FR | 2743293 | 7/1997 |
| JP | A-H08-501471 | 2/1996 |
| JP | A-H10-507382 | 7/1998 |
| JP | A-2009-504349 | 2/1999 |
| JP | A-H11-501243 | 2/1999 |
| JP | A-2000-185105 | 7/2000 |
| JP | A-2008-539050 | 1/2008 |
| JP | A-2008-518710 | 6/2008 |
| WO | WO-9319703 | 10/1993 |
| WO | WO-9632077 | 10/1996 |
| WO | 9844873 A1 | 10/1998 |
| WO | WO-9852496 | 11/1998 |
| WO | WO-9855047 | 12/1998 |
| WO | 0103762 A1 | 1/2001 |
| WO | WO-0105332 | 1/2001 |
| WO | WO-0152770 | 7/2001 |
| WO | WO-03084439 | 10/2003 |
| WO | WO-2005112823 | 12/2005 |
| WO | WO-2006116725 | 11/2006 |
| WO | WO-2008005535 | 1/2008 |
| WO | 2009085186 A1 | 7/2009 |
| WO | WO-2009132309 | 10/2009 |
| WO | WO-2009/140638 | 11/2009 |
| WO | 2010127040 A1 | 11/2010 |
| WO | WO-2010/132836 | 11/2010 |
| WO | WO-2011003019 | 1/2011 |
| WO | WO-2011049808 | 4/2011 |
| WO | WO-2011068915 | 6/2011 |
| WO | WO-2012040240 | 3/2012 |
| WO | 2012088888 A1 | 7/2012 |
| WO | WO-2012128846 | 9/2012 |

OTHER PUBLICATIONS

U.S. Appl. No. 12/958,374, filed Dec. 1, 2010, Cragg et al.
U.S. Appl. No. 12/958,378, filed Dec. 1, 2010, Cragg et al.
U.S. Appl. No. 12/958,381, filed Dec. 1, 2010, Cragg et al.
U.S. Appl. No. 12/958,383, filed Dec. 1, 2010, Cragg et al.
U.S. Appl. No. 13/963,912, filed Aug. 9, 2013, Cragg et al.
U.S. Appl. No. 13/964,013, filed Aug. 9, 2013, Cragg et al.
U.S. Appl. No. 61/053,378, filed May 15, 2008, Cragg et al.
U.S. Appl. No. 61/265,713, filed Dec. 1, 2009, Cragg et al.
U.S. Appl. No. 61/293,581, filed Jan. 8, 2010, Cragg et al.
U.S. Appl. No. 61/311,735, filed Mar. 8, 2010, Cragg et al.
U.S. Appl. No. 61/320,646, filed Apr. 2, 2010, Cragg et al.
U.S. Appl. No. 61/384,669, filed Sep. 20, 2010, Cragg et al.
Australian Patent Examination Report No. 1, Australian Patent Application No. 2012203709; dated Jan. 30, 2013; 4 pages.
Australian Patent Examination Report No. 1, Australian Patent Application No. 2012203705; dated Jan. 31, 2013; 4 pages.
Australian Patent Examination Report No. 1, Australian Patent Application No. 2012203708; dated Feb. 1, 2013; 5 pages.
Beebe, H.G.; "Imaging Modalities for Aortic Endografting"; J Endovasc Surg; May 1997; vol. 4, Issue 2, pp. 111-123 (20 pages).

(56) References Cited

OTHER PUBLICATIONS

Brewster, DC; "Initial Experience with Endovascular Aneurysm Repair: Comparison of Early Results with Outcome of Conventional Open Repair"; J Vasc Surg; Jun. 1998; vol. 27, Issue 6, pp. 992-1003; discussion 1004-5 (14 pages).
Cao, P.; "Comparison of Surveillance vs. Aortic Endografting for Small Aneurysm Repair (CAESAR) Trial: Study Design and Progress"; Eur. J. Vasc. Endovasc. Surg.; Sep. 2005; vol. 30, Issue 3; pp. 245-251 (7 pages).
Dorros, G. et al.; "Evaluation of Endovascular Abdominal Aortic Aneurysm Repair: Anatomical Classification, Procedural Success, Clinical Assessment, and Data Collection"; J. Endovasc Surg; May 1997; vol. 4, Issue 2; pp. 203-225 (24 pages).
Dosluoglu et al.; "Total Percutaneous Endovascular Repair of Abdominal Aortic Aneurysms Using Perclose ProGlide Closure Devices"; J. Endovasc Ther.; Apr. 2007, vol. 14, Issue 2, pp. 184-188 (5 pages).
Faries, P.L.; "Endovascular Stent Graft Selection for the Treatment of Abdominal Aortic Aneurysms"; J. Cardiovasc Surg (Torino); Feb. 2005; vol. 46, Issue 1, pp. 9-17 (9 pages).
Final Office Action; U.S. Appl. No. 12/466,044; dated Sep. 14, 2012; 9 pages.
Final Office Action; U.S. Appl. No. 12/628,131; dated Nov. 21, 2012; 19 pages.
Final Office Action; U.S. Appl. No. 12/958,383; dated Jan. 9, 2013; 29 pages.
Final Office Action; U.S. Appl. No. 12/958,381; dated Jan. 31, 2013; 36 pages.
International Search Report and Written Opinion, PCT/US09/44212, Mailed on Jul. 14, 2009, Applicant: Altura Medical, Inc., 11 pages.
International Search Report and Written Opinion, PCT/US10/58621, Mailed on Feb. 9, 2011, Applicant: Altura Medical, Inc., 33 pages.
International Search Report and Written Opinion, PCT/US2010/035003, Mailed on Feb. 9, 2011, Applicant: Altura Medical, Inc., 10 pages.
International Search Report and Written Opinion, PCT/US2011/052412, Mailed on Jan. 17, 2012, Applicant: Altura Medical, Inc., 9 pages.
Kahraman, H. et al., "The Diameters of the Aorta and Its Major Branches in Patients with Isolated Coronary Artery Ectasia," Texas Heart Institute Journal; 2006, vol. 33, No. 4, pp. 463-468.
Laborde, J.C. et al., "A Novel 14F Endograft for Abdominal Aortic Aneurysm: First in Man," *Catheterization and Cardiovascular Interventions*, Jun. 2010 (20 pages).
Laborde, J.C. et al., "Intraluminal Bypass of Abdominal Aortic Aneurysm: Feasibility Study"; Radiology; Jul. 1992; vol. 184, Issue 1; pp. 185-190 (6 pages).
Mathison, M.N.; "Implications of Problematic Access in Transluminal Endografting of Abdominal Aortic Aneurysm"; J Vasc Intery Radiol; Jan. 2003; vol. 14, Issue 1, pp. 33-39 (7 pages).
Matsumura, J.S.; "A Multicenter Controlled Clinical Trial of Open Versus Endovascular Treatment of Abdominal Aortic Aneurysm"; J Vasc Surg; Feb. 2003; vol. 37, Issue 2, pp. 262-271 (13 pages).
Non-Final Office Action, U.S. Appl. No. 12/466,044, dated May 7, 2012, 35 pages.
Non-Final Office Action, U.S. Appl. No. 12/628,131, dated May 11, 2012, 20 pages.
Non-Final Office Action, U.S. Appl. No. 12/958,367, dated Aug. 17, 2012, 28 pages.
Non-Final Office Action, U.S. Appl. No. 12/958,374, dated Aug. 16, 2012, 28 pages.
Non-Final Office Action, U.S. Appl. No. 12/958,378, dated Aug. 16, 2012, 25 pages.
Non-Final Office Action, U.S. Appl. No. 12/958,381, dated Aug. 9, 2012, 30 pages.
Non-Final Office Action, U.S. Appl. No. 12/958,383, dated Aug. 16, 2012, 28 pages.
Non-Final Office Action, U.S. Appl. No. 12/466,044, dated Jan. 3, 2013, 12 pages.
Parodi, J.C. et al., "Transfemoral Intraluminal Graft Implantation for Abdominal Aortic Aneurysms", Ann Vasc Surg.; Nov. 1991; vol. 5, Issue 6, pp. 491-499 (9 pages).
Powell, J.T. et al.; "Final 12-year Follow-up of Surgery Versus Surveillance in the UK Small Aneurysm Trial"; Br. J. Surg.; Jun. 2007; vol. 94, Issue 6, pp. 702-708 (7 pages).
Volodos, N.L. et al.; "Clinical Experience of the use of Self-Fixing Synthetic Prostheses for Remote Endoprosthetics of the Thoracic and the Abdominal Aorta and Iliac Arteries Through the Femoral Artery and as Intraoperative Endoprosthesis for Aorta Reconstruction"; Kharkov Research Institute of General and Urgent Surgery; J. Vasc. Diseases-Suppl.; 1991; vol. 33, pp. 93-95 (5 pages).
Zarins, C.K.; "AneuRx Stent Graft Versus Open Surgical Repair of Abdominal Aortic Aneurysms: Multicenter Prospective Clinical Trial"; J Vasc Surg; Feb. 1999; vol. 29, Issue 2, pp. 292-308 (19 pages).
Zarins C.K.; "Endovascular Repair or Surveillance of Patients with Small AAA"; Eur. J. Vasc. Endovasc. Surg.; May 2005; vol. 29, Issue 5; pp. 496-503; located at www.sciencedirect.com (9 pages).
Dereume, J.P. et al., "Endoluminal Treatment of Abdominal Aortic Aneurysm with the Corvita Endovascular Graft. Results of a Single-Center, Prospective Feasibility Study of 90 Patients," Journal of Endovascular Surgery; Nov. 1996, vol. 3, 1 page.
Chinese Preliminary Examination Report; Chinese Patent Application No. 100876, mailed on Mar. 30, 2012, 1 page.
Australian Patent Examination Report No. 1, Australian Patent Application No. 2012203707, mailed on Jan. 31, 2013, 4 pages.
Sanchez, Luis et al., "Early Experience with the Corvita Endoluminal Graft for Treatment of Arterial Injuries," From the Divisions of Vascular Surgery and Interventional Radiology, Montefiore Medical Center, New York. Presented May 31, 1997, 7 pages.
Sitsen, M. et al., "Deformation of Self-Expanding Stent-Grafts Complicating Endovascular Peripheral Aneurysm Repair," J Endovascular Surgery, 1999. 5 pages.
Non-Final Office Action, U.S. Appl. No. 13/237,822, mailed on Dec. 5, 2013, 11 pages.
Japanese Office Action, Japanese Application No. 2012-511058, mailed on Mar. 3, 2014, 38 pages.
Australian Patent Examination Report No. 1, Australian Patent Application No. 2009246093; dated Jan. 31, 2014; 4 pages.
Australian Patent Examination Report No. 1, Australian Patent Application No. 2010248822; dated Nov. 26, 2014; 3 pages.
Australian Patent Examination Report No. 1, Australian Patent Application No. 2010326046; dated Feb. 27, 2015; 2 pages.
Chinese Office Action 1; Chinese Patent Application No. 200980126821.7, mailed Apr. 3, 2013, 12 pages.
Chinese Office Action 1; Chinese Patent Application No. 201080031916.3, mailed Jan. 16, 2014, 12 pages.
Chinese Office Action 2; Chinese Patent Application No. 200980126821.7, mailed Dec. 24, 2013, 11 pages.
Extended European Search Report, European Application No. 12174632.5, dated Sep. 26, 2014, 7 pages.
Extended European Search Report, European Application No. 12174641.6, dated Sep. 29, 2014, 7 pages.
Extended European Search Report, European Application No. 12174645.7, dated Sep. 29, 2014, 5 pages.
Extended European Search Report, European Application No. 12174647.3, dated Sep. 29, 2014, 9 pages.
Final Office Action, U.S. Appl. No. 12/466,044, mailed on May 29, 2013, 14 pages.
Final Office Action; U.S. Appl. No. 12/958,367; dated Mar. 28, 2013; 27 pages.
Final Office Action; U.S. Appl. No. 12/958,374, mailed Apr. 1, 2013, 26 pages.
Final Office Action; U.S. Appl. No. 12/958,378; dated Mar. 29, 2013; 35 pages.
International Search Report and Written Opinion, PCT/US2014/029373, Mailed on Aug. 12, 2014, Applicant: Altura Medical, Inc., 14 pages.

(56) References Cited

OTHER PUBLICATIONS

Japanese Office Action, Japanese Application No. 2012-511058, mailed on Jan. 7, 2015, 8 pages.
Japanese Office Action; Japanese Patent Application No. 2011-509771, mailed Jul. 10, 2013, 5 pages.
Non-Final Office Action, U.S. Appl. No. 12/628,131, dated Feb. 13, 2014 15 pages.
Non-Final Office Action, U.S. Appl. No. 12/958,367, dated Dec. 16, 2014, 28 pages.
Non-Final Office Action, U.S. Appl. No. 12/958,374, dated Dec. 3, 2014, 24 pages.
Non-Final Office Action, U.S. Appl. No. 12/958,383, dated Apr. 13, 2015, 45 pages.
Non-Final Office Action; U.S. Appl. No. 13/964,015; dated Dec. 29, 2014; 16 pages.
Final Office Action, U.S. Appl. No. 12/466,044, mailed on Jun. 19, 2014, 15 pages.
Chinese Office Action, Chinese Application No. 2009801268217, mailed May 7, 2014, 12 pages.
Japanese Office Action; Japanese Patent Application No. 2011-509771, mailed May 28, 2014, 10 pages.
Non-Final Office Action; U.S. Appl. No. 12/958,383, mailed on Jul. 31, 2014, 45 pages.
International Search Report and Written Opinion; App. No. PCT/US2013/054438, mailed on Feb. 7, 2014, Applicant: Andrew H. Cragg, 23 pages.
Final Office Action, U.S. Appl. No. 12/628,131, mailed on Oct. 8, 2014, 20 pages.
Non-Final Office Action; U.S. Appl. No. 12/958,381, mailed on Oct. 3, 2014, 17 pages.
Chinese Office Action, Chinese Application No. 200980126821.7, mailed Sep. 11, 2014, 5 pages.
Chinese Office Action, Chinese Application No. 201080062913.6, mailed on Nov. 15, 2014, 13 pages.
Japanese Office Action, Japanese Application No. 2012-542171, mailed on Sep. 24, 2014, 2 pages.

* cited by examiner

ENDOGRAFT DEVICE DELIVERY SYSTEMS AND ASSOCIATED METHODS

CROSS-REFERENCE TO RELATED APPLICATION(S)

This application claims the benefit of U.S. Provisional Patent Application No. 61/786,364, filed Mar. 15, 2013, the disclosure of which is incorporated herein by reference in its entirety.

TECHNICAL FIELD

The present technology generally relates to endograft devices and methods for percutaneous endovascular delivery of such endograft devices across aneurysms. In particular, several embodiments of the present technology are directed toward delivery devices for a modular bi-luminal endograft device with independently positioned components for endovascular aneurysm repair, and an associated delivery system and method for delivering the endograft device in desired alignment with a renal artery.

BACKGROUND

An aneurysm is a dilation of a blood vessel at least 1.5 times above its normal diameter. A dilated vessel can form a bulge known as an aneurysmal sac that can weaken vessel walls and eventually rupture. Aneurysms are most common in the arteries at the base of the brain (i.e., the Circle of Willis) and in the largest artery in the human body, the aorta. The abdominal aorta, spanning from the diaphragm to the aortoiliac bifurcation, is the most common site for aortic aneurysms. The frequency of abdominal aortic aneurysms ("AAAs") results at least in part from decreased levels of elastins in the arterial walls of the abdominal aorta and increased pressure due to limited transverse blood flow.

Aneurysms are often repaired using open surgical procedures. Surgical methods for repairing AAAs, for example, require opening the abdominal region from the breast bone to the pelvic bone, clamping the aorta to control bleeding, dissecting the aorta to remove the aneurysmal section, and attaching a prosthetic graft to replace the diseased artery. The risks related to general anesthesia, bleeding, and infection in these types of open surgical repairs result in a high possibility of operative mortality. Thus, surgical repair is not a viable option for many patients. Moreover, the recovery process is extensive for the patients fit for surgical repair. An open surgical repair of an AAA generally requires seven days of post-operational hospitalization and, for uncomplicated operations, at least six to eight weeks of recovery time. Thus, it is a highly invasive and expensive procedure.

Minimally invasive surgical techniques that implant prosthetic grafts across aneurysmal regions of the aorta have been developed as an alternative or improvement to open surgery. Endovascular aortic repairs ("EVAR"), for example, generally require accessing an artery (e.g., the femoral artery) percutaneously or through surgical cut down, introducing guidewires into the artery, loading an endograft device into a catheter, and inserting the loaded catheter in the artery. With the aid of imaging systems (e.g., X-rays), the endograft device can be guided through the arteries and deployed from a distal opening of the catheter at a position superior to the aneurysm. From there, the endograft device can be deployed across the aneurysm such that blood flows through the endograft device and bypasses the aneurysm.

EVAR devices should be implanted at a precise location across the aneurysmal region and securely fixed to the vessel wall because improper placement, migration, and/or projection of the endograft device into branching vessels may interfere with the blood flow to nearby physiological structures. For example, to avoid impairing renal functions, the endograft device should not inhibit blood flow to the renal arteries. In addition to the variations in the vasculature between patients, the characteristics of the aneurysms themselves can also pose challenges because of the anatomical variations and the different structural features of individual aneurysms. For example, the vascular bifurcation at the iliac arteries and the angulation of aneurysmal sacs are both known to pose challenges to methods and devices for treating AAAs. Many conventional systems address these challenges by requiring that hospitals/clinics maintain significant inventories of different EVAR devices with different sizes and shapes.

DETAILED DESCRIPTION

Figure 1A:
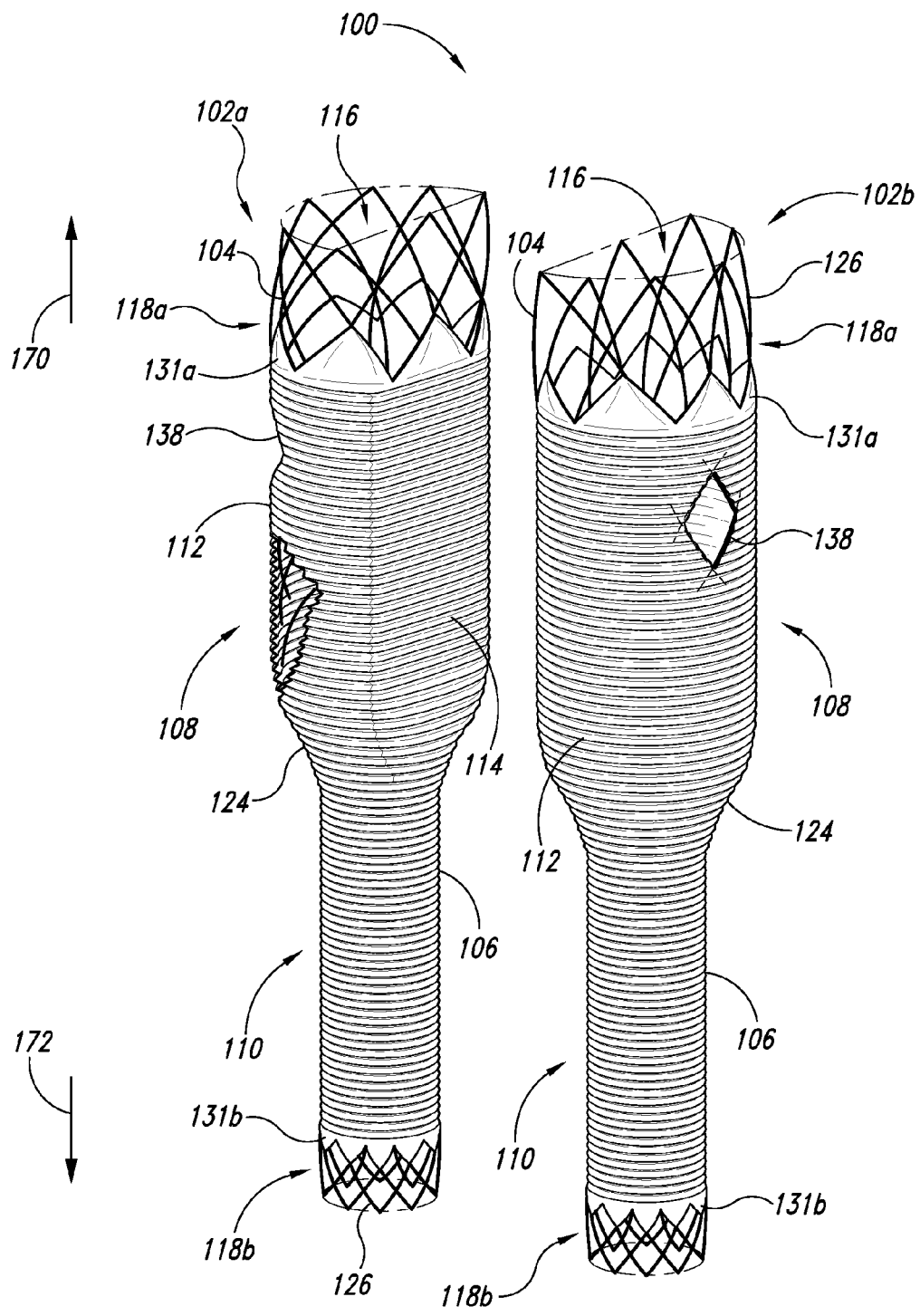
FIG. 1A is a partial cut-away, isometric view of a modular endograft system configured in accordance with an embodiment of the technology.

The present technology is directed toward endograft devices and methods for percutaneous endovascular delivery of endograft devices across aneurysms. In particular, several embodiments of the present technology are directed toward delivery devices for a modular bi-luminal endograft device with independently positioned components for endovascular aneurysm repair, and associated delivery systems and methods for delivering the endograft device in desired alignment with renal arteries of the patient. As compared with conventional endograft devices, various embodiments of the present technology are expected to provide improved sealing between the endograft device and healthy vascular tissue on each side of the AAA or vascular defect. Endograft devices configured in accordance with the present technology are also expected to provide enhanced control of the rotational and axial position of the device when placing the device within the vasculature, thereby enabling such devices to achieve sufficient sealing and bridging of the AAA or vascular defect.

Certain specific details are set forth in the following description and in FIGS. 1A-3F to provide a thorough understanding of various embodiments of the technology. For example, many embodiments are described below with respect to the delivery of stent grafts that at least partially repair AAAs. In other applications and other embodiments, however, the technology can be used to repair aneurysms in other portions of the vasculature. Other details describing well-known structures and systems often associated with endografts and associated delivery devices and procedures have not been set forth in the following disclosure to avoid unnecessarily obscuring the description of the various embodiments of the technology. A person of ordinary skill in the art, therefore, will accordingly understand that the technology may have other embodiments with additional elements, or the technology may have other embodiments without several of the features shown and described below with reference to FIGS. 1A-3F.

In this application, the terms "distal" and "proximal" can reference a relative position of the portions of an implantable device and/or a delivery device with reference to an operator. Proximal refers to a position closer to the operator of the device, and distal refers to a position that is more distant from the operator of the device.

The terms "inferior" within this application generally refers to being situated below or directed downward, and the term "superior" generally refers to being situated above or directed upward.

In this application, the term "expansion" refers to a radial increase in a cross-sectional dimension of a device or component, and the term "constriction" refers to a radial decrease in the cross-sectional dimension of the device or component. For example, FIGS. 1A and 1B show an integrated frame 104 in an expanded configuration, and FIG. 2 shows the integrated frame 104 in a constricted configuration.

The term "extension" also refers to a longitudinal increase in the length of the device or component, while the term "contraction" refers to a longitudinal decrease in the length of a device or component.

1. Endograft System Structures

Figure 1B:
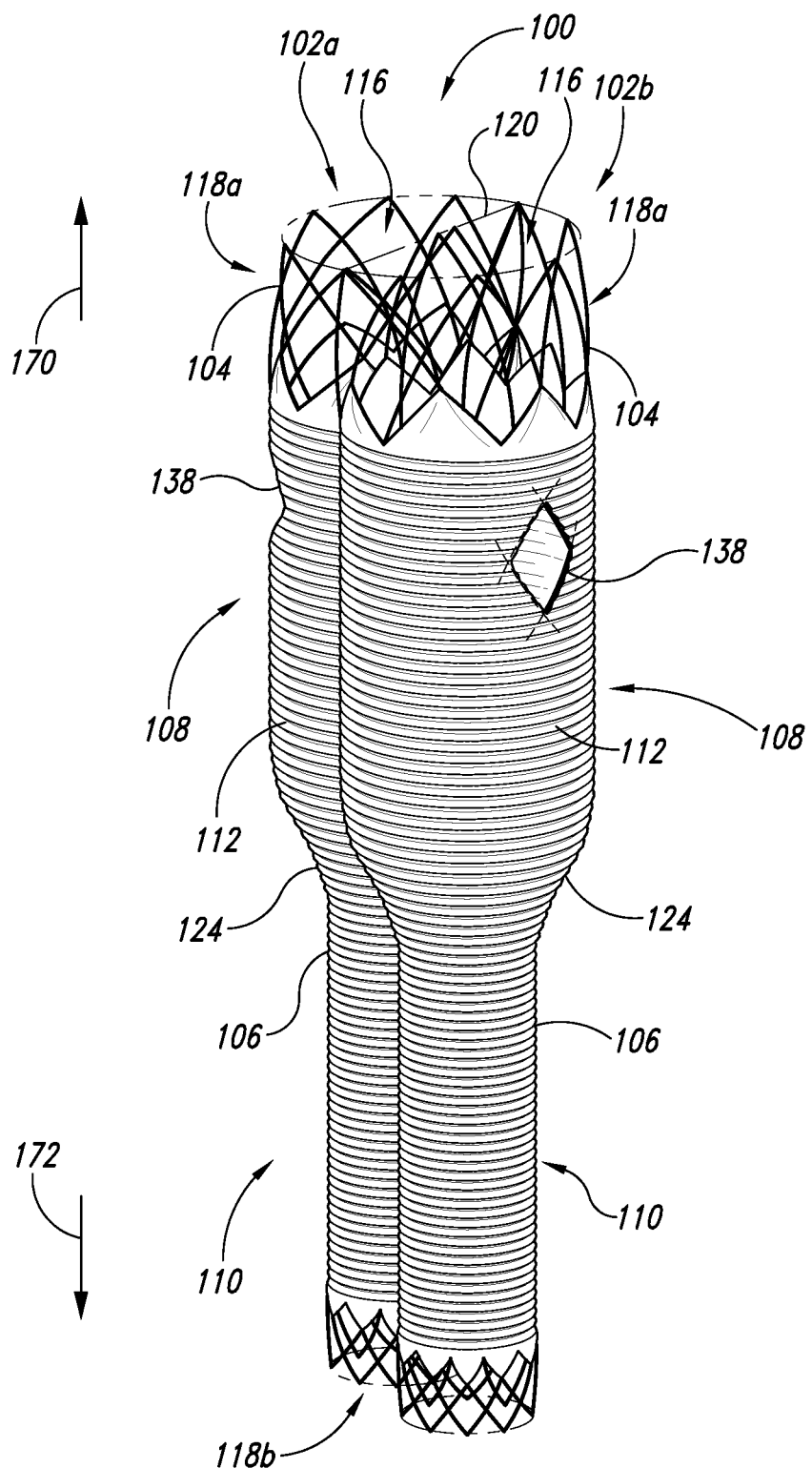
FIG. 1B is an isometric view of the modular endograft system of FIG. 1A configured in accordance with an embodiment of the technology.
Figure 2:
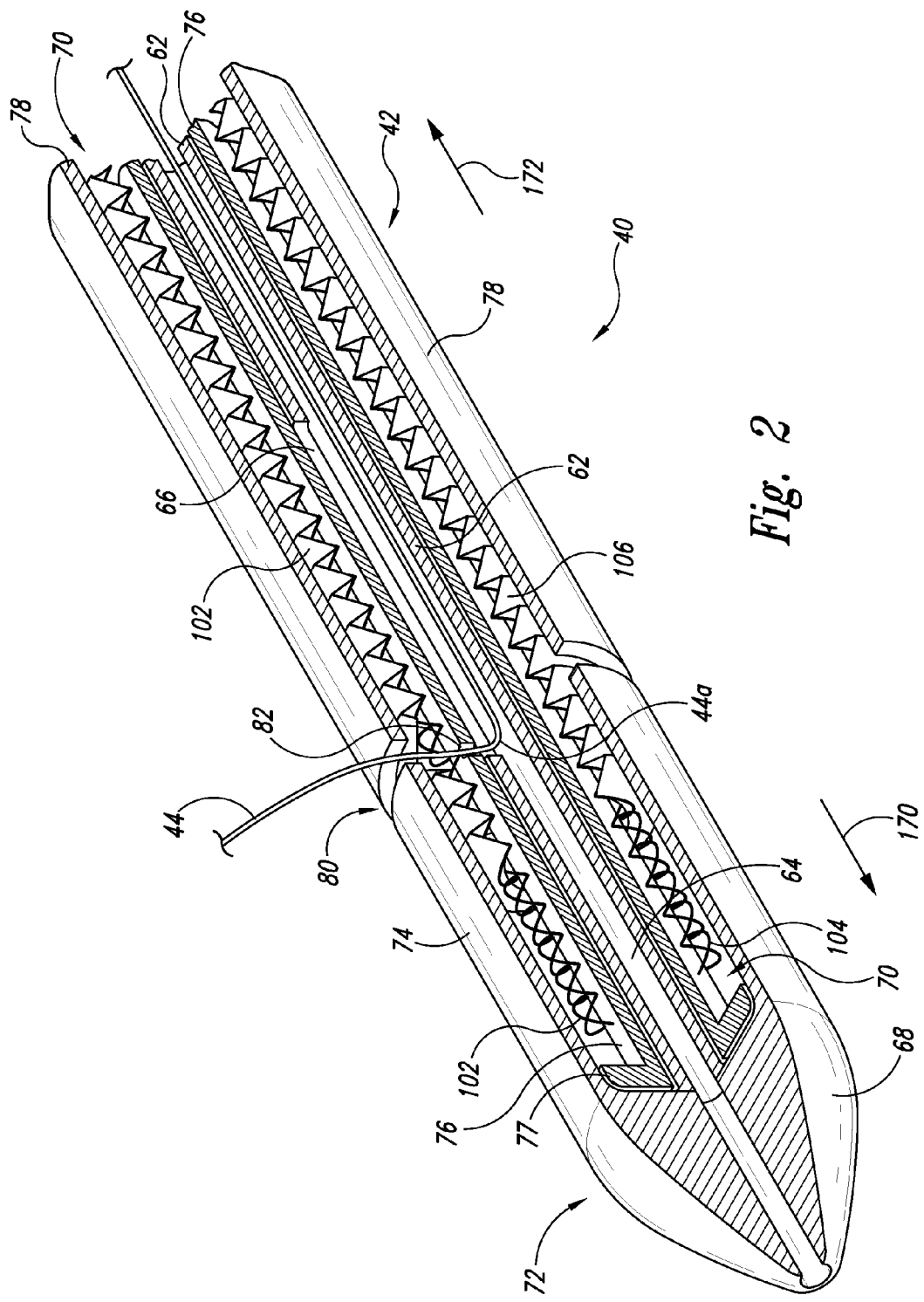
FIG. 2 is a partial cross-sectional view of an endograft delivery system configured in accordance with embodiments of the technology.

FIGS. 1A and 1B are isometric views of a modular endograft system 100 ("system 100") configured in accordance with an embodiment of the technology. The system 100 can include separate endograft devices or endografts 102 (identified individually as a first endograft device 102a and a second endograft device 102b) that can be coupled, mated, or otherwise substantially sealed together in situ. The first and second endograft devices 102a and 102b can be identical or essentially identical to each other (as shown in FIGS. 1A and 1B) or, as described further below, have some different structural features that provide a system 100 having one endograft device 102 embodying the present technology and another endograft device that differs from the present technology (generically referred to as a "vascular device" for clarity). Each endograft device 102, for example, can include an integrated frame 104 ("frame 104") and a substantially impermeable cover 106 ("cover 106") extending over at least a portion of the frame 104 (revealed in the cut-away view presented in FIG. 1A in the middle of endograft 102a). The frame 104 and the cover 106 of an individual endograft device 102 can form a discrete lumen 116 through which blood can flow to bypass an aneurysm. In operation, the endograft devices 102 (or the endograft device 102 and a vascular device) are generally delivered to a implant target site separately and positioned independently across the aneurysm.

As shown in FIGS. 1A and 1B, each endograft device 102 includes a superior portion 108 and an inferior portion 110. The superior portion 108 can include a convexly curved outer wall 112 and a septal wall 114. As shown in FIG. 1A, the septal wall 114 can be substantially flat such that the superior portion 108 forms a "D" shape at a superior portion of the lumen 116. In other embodiments, the septal wall 114 can be convexly curved with a larger radius of curvature than the outer wall 112 such that the superior portion 108 forms a complex ellipsoid having another D-shaped cross-section at the superior portion of the lumen 116. In further embodiments, the superior portion 108 can have asymmetrical shapes or other suitable cross-sectional configurations that can mate with each other in the septal region and mate with an arterial wall around the periphery of the outer wall 112. The inferior portion 110 can have a circular cross-sectional shape as illustrated in FIG. 1A, or the inferior portion 110 can have an elliptical shape, a rectangular shape, an asymmetrical shape, and/or another suitable cross-sectional shape for an inferior portion of the lumen 116.

Referring to FIG. 1B, the superior portions 108 of the endograft devices 102 are mated together and at least substantially sealed along the septal walls 114 within the aorta above the aneurysm. In some embodiments, the superior portion 108 can be approximately 2-4 cm in length to adequately fix the outer walls 112 to the arterial walls such that they are at least substantially sealed together. In other embodiments, the superior portion 108 can be longer or shorter. In one embodiment in accordance with the technology, the inferior portions 110 can extend through an inferior portion of the aneurysm and into corresponding iliac arteries to bypass the aneurysm. In another embodiment, one or both inferior portions 110 can terminate within the aneurysm to form what is known to those skilled in the art as a "gate." As described in commonly owned U.S. application Ser. No. 12/958,367, incorporated herein by reference in its entirety, limbs (not shown) can be attached to the proximal ends of the inferior portions 110 and extended into the iliac arteries to bypass the aneurysm.

In the embodiment shown in FIGS. 1A and 1B, the frames 104 have bare end portions 118 (identified individually as first end portions 118a and second end portions 118b) that extend beyond the covers 106. As shown in FIGS. 1A and 1B, the first end portion 118a can extend distally (in distal direction 170) from the superior terminus of the cover 106, and the second end portion 118b can extend proximally (in proximal direction 172) from the inferior terminus of the cover 106. In some embodiments, the end portions 118 can be trumpeted or flared to interface with the arterial walls of the aorta and/or the iliac arteries. This can promote cell ingrowth that strengthens the seal between the endograft devices 102 and the adjacent arteries.

Referring to FIGS. 1A and 1B, each endograft device 102 can also include a fenestration 138 configured in accordance with embodiments of the technology. The fenestration(s) 138, for example, can be openings that provide communication to the interior lumen 116 through the frame 104 and cover 106 and provide a channel through which blood flow can be shared with transverse arteries. In other embodiments, the fenestration 138 may comprise a slot that extends from a single opening of the frame 104 (intended for alignment with a renal artery) to the termini of the cover 106, which is a configuration that leaves several opening through the frame exposed (i.e., without a cover 106) but disposed to engage the vascular wall to prevent leakage to or from the lumen 116. The fenestration(s) 138 can be formed, for example, by cutting the cover 106 in a desired location to form a passage through the cover 106 and the underlying frame 104. The edges of the cover 106 defining the fenestration 138 can be secured to the frame 104 by, for example, sutures or glue. In still other embodiments, however, other suitable techniques may be used to form each fenestration 138. The cutting and/or the securing can be done (a) immediately prior to the implantation of the corresponding endograft 102; (b) while the corresponding endograft 102 is in the low-profile position within a delivery chamber of a delivery catheter (as described in greater detail below with reference to FIG. 2); or (c) while the corresponding endograft 102 is partially expanded and accessible through a portion of the delivery catheter before being returned to a low-profile configuration for implantation (as also described in greater detail below with reference to FIG. 2).

The fenestration(s) 138 may be positioned at an angle relative to the septal wall 114 of the endograft 102 or relative to the septum 120 provided by the mating of two endografts 102 (as best seen in FIG. 1B). The angle of the fenestration(s) 138, for example, may be based on an anatomical angulation/arrangement of a transverse vessel such that, when the endograft 102 is implanted, the fenestration 138 is generally centered relative to an opening of the transverse vessel. The particular anatomy at the implant target site may be determined, for example, using suitable imaging techniques.

In some embodiments, two mating endografts 102 including fenestrations 138 may define a fenestration axis passing through a middle of each fenestration. The two fenestrations 138, for example, can be opposed to each other so that the two fenestration axes are the same axis. In other embodiments, however, the two fenestration axes may offset from each other with one disposed more in the distal direction 170 than the other such that the two fenestration axes define an angle between them that is not 180 degrees, or such that the two fenestrations axes have any combination of the aforementioned configurations. In this configuration, the clinical operator can choose an endograft device or pair of endograft devices having the appropriate circumferential offset to match the renal artery orientation of a given patient. In another configuration, the endograft device can include multiple circumferentially offset (e.g., radially disposed) fenestrations to better enable the clinical operator to align one of the fenestrations with the branch renal vessel. In this configuration, for example, the endograft device might have two, three, four, or more fenestrations circumferentially offset by a suitable angle (e.g., 15 degrees, 30 degrees, 45 degrees 60 degrees).

In another configuration, the endograft device can have a fenestration covered by a fabric flap, wherein the flap can be opened (with or without stenting) or removed to create the fenestration. If unused, the flap can be replaced and/or remain closed to maintain a sealed surface. Additionally or alternatively, the endograft device can include one or more slits horizontally or vertically disposed relative to the longitudinal axis of the endograft. Such a slit can be opened (e.g., via stenting) to create a fenestration and enable perfusion via a branch vessel. If oriented horizontally, the slit could extend substantially around the perimeter of the convexly curved outer wall to allow for incremental change in orientation due to variations in renal artery anatomy. If oriented vertically, the slit could extend axially to optimize axial orientation.

As described in greater detail below with reference to FIGS. 3A-3F, the location of the fenestration(s) 138 may be customized for patients to correspond to the positions of renal arteries of the patient (e.g., as observed by an imaging system before the implant procedure). For example, each fenestration 138 can be positioned on the cover 106 proximal to the first end portion 118a to increase the portions of the endograft 102 extending distal to the renal artery to provide improved contact between the endograft 102 and the arterial wall. The arrangement of the fenestration(s) 138 through the cover 106 also maximizes the portion of the endograft 102 having both a frame 104 and a cover 106 located between the renal artery and the aneurysm, which is believed to provide an improved seal and provide greater flexibility in adapting the endograft device 102 to unique anatomies.

In another embodiment, the endograft design may allow for one or more preformed or preshaped fenestrations. For example, due to the density of the braid design, the endograft and fenestration positioned therein would be able to retain its original shape and fenestration position following delivery and deployment, thereby making for more reliable positioning. The braid density may also enable more complex fenestration shapes to accommodate anatomical variability and challenges. For example, the endograft devices described herein can be configured with one or more preformed troughs at the apex of the convexly curved outer wall of the superior portion to allow the positioning of a "chimney" stent graft for perfusion to the renal artery or other branch vessels.

2. Endograft System Deployment

During deployment of the system 100, each endograft device 102 can be delivered independently to an aneurysmal region in a low-profile configuration (e.g., as described in further detail with reference to FIG. 2 below). The low-profile configuration has a first cross-sectional dimension and a first length that can facilitate percutaneous endovascular delivery of the system 100. Because each device 102 extends around only a portion of the vessel periphery, the individual endograft devices 102 can be constricted (i.e., radially collapsed) to a smaller diameter than conventional AAA devices with a single superior portion that extends around the complete periphery of the vessel wall. In some embodiments, for example, each of the endograft devices 102 can have a diameter of approximately 25 mm in the expanded configuration, and can be constricted to a diameter of approximately 4 mm in the low-profile configuration to be percutaneously deployed across the aneurysm through a 12 F catheter. Additionally, as described in more detail below, because each endograft device 102 is delivered independently, the end portions 118 can facilitate staggering of the endograft devices 102 to accommodate asymmetrical anatomies, with one endograft device 102 disposed more in the distal direction than the mating endograft device 102 or vascular device.

At an implant target site in the aneurysmal region, the endograft devices 102 can self-expand from the low-profile configuration to an expanded configuration (e.g., as shown in FIGS. 1A and 1B). The expanded configuration can have a second cross-sectional dimension greater than the first cross-sectional dimension and a second length less than the first length. In the expanded configuration shown in FIG. 1B, for example, the septal wall 114 (FIG. 1A) of the first endograft device 102a can be forced against the opposing septal wall 114 of the second endograft device 102b. When in situ within the aorta, the forces between the opposing septal walls 114 form a septum 120 in which the first and second septal walls 114 are at least substantially sealed together to prevent blood from flowing between the endograft devices 102 and into the aneurysm. Additionally, as shown in FIG. 1B, the texture (e.g., ribbing) on the covers 106 can mate at the septum 120 to further strengthen the seal between the septal walls 114. Similarly, the texture of the cover 106 on the outer walls 112 can interface with the adjacent vessel walls to strengthen the seal around the periphery of the endograft devices 102.

As described above, each endograft device 102 can include the fenestration 138 as shown in FIGS. 1A and 1B, providing communication through the frame 104 and cover 106 proximally to the end portions 118 so as to provide greater flexibility in adapting the endograft device 102 to unique anatomies. During deployment, for example, the fenestrations 138 in combination with the end portion 118 can increase the available structure for securing the endograft devices 102 to the artery and increase the available surface area for sealably fixing the endograft device 102 to arterial walls. This increase in available endograft structure at the ends of the endograft device 102 is expected to decrease the precision necessary to position the endograft device 102, while increasing the reliability of the implanted system 100.

In operation, the system 100 is configured to prevent blood from collecting in a diseased aneurysmal portion of a blood vessel (e.g., the aorta, the iliac arteries, etc.). Rather, the system 100 directs blood into the lumens 116, funnels the blood through the superior and inferior portions 108 and 110, and discharges the blood into healthy portions of the iliac arteries, thereby at least substantially bypassing the aneurysm. As noted previously, the bifurcated system 100 facilitates independent positioning of the first and second endograft devices 102 to accommodate disparate structures and morphologies of the abdominal aorta and/or iliac arteries. For example, the first endograft device 102a can be positioned independently in a desired location without being constrained by a desired placement of the second endograft device 102b. Furthermore, in another example, the selection and placement of the fenestrations 138 on either or both of the endograft devices 102 can be made to conform with patient anatomy thereby allowing greater control in how each of the endograft devices 102 are positioned relative to unique patient anatomy. Accordingly, the system 100 can easily adapt to a variety of different anatomies and thereby provide a modular alternative to customized endograft systems.

3. Endograft Delivery System

FIG. 2 is a partial cross-sectional view of a delivery system 40 configured in accordance with an embodiment of the technology. For clarity, the delivery system 40 in FIG. 2 has been illustrated to have an overly-short axial length and an overly-large diameter so as to better show the axial and radial arrangement of components in a single FIGURE; it will be appreciated, however, that a delivery device 40 sized for use with, for example, the endografts 102 of FIGS. 1A and 1B, would have a significantly longer and thinner appearance). The delivery system 40 can include a catheter 42 configured for delivery via a guidewire 44, and can be used to deliver and deploy the endograft 102 at the implant target site. The catheter 42 can have a distal end configured to deliver the endograft 102 as shown in FIG. 2 and a proximal end (not shown) configured to be manipulated by an operator (not shown) to control delivery of the endograft 102. The distal end of the catheter 42 can have an inner tube 62 with a distal end of the inner tube 62 connected to a nose cone 72 having a distal end with a tapering tip 68 and a proximal end with a cup-like shape and a peripheral cylindrical wall 74 that extends in the proximal direction 172 to define a first internal volume within the cylindrical wall that encloses part of the distal end of the inner tube 62. The distal end of the catheter 42 can also have a pusher tube 76 enclosing the inner tube 62 within an internal lumen of the pusher tube 76, with a distal end of the pusher tube 76 having an abutment 77 disposed within the cylindrical wall 74. The distal end of the catheter 42 can also include a sheath 78 enclosing the pusher tube 76. A distance between the distal end of the sheath 78 and the pusher tube 76 defines a second internal volume. The first and second internal volumes can together provide a delivery chamber 70 for holding the endograft 102 in a low-profile configuration with a distal end of the endograft 102 releasably held by the cylindrical wall 74 and a proximal end of the endograft 102 releasably held by the sheath 78. The delivery chamber 70 is defined, at least in part, by the pusher tube 76, the abutment 77 of the pusher tube 76, the cylindrical wall 74, and the sheath 78.

As shown in FIG. 2, the guidewire 44 includes a distal portion extending from the distal end of the catheter 42 and a proximal portion extending though the inner lumen 64 in the proximal direction 172. As shown, the guidewire 44 can pass through the catheter 42 and the endograft 102 carried within the delivery chamber 70 along a guidewire path defined by the catheter 42 and the endograft 102. The guidewire path can have one end where the distal end of the guidewire 44 enters the catheter 42 between the cylindrical wall 74 and the sheath 78. The cylindrical wall 74 can provide an edge on the proximal surface of the cylindrical wall 74 that is positioned to face, abut, or overlap a distal edge of the sheath 78 to define a separation 80 between the sheath 78 and the cylindrical wall 74 of the nose cone 72. The guidewire path can continue into the distal end of the catheter 42 and can pass through a fenestration 138 of the endograft 102 (see FIGS. 1A and 1B) and then lead into a transverse opening 82 passing through the side of the pusher tube 76 to enter the lumen of the pusher tube. The guidewire path can continue on to pass through the transverse slot 66 of the inner tube 62 and enter the inner lumen 64. As shown in FIG. 2, the guidewire 44 can have a bend 44a where the orientation of the guidewire 44 changes from an coaxial direction along the length of the catheter 42 within the inner lumen 64 to a transverse direction passing out of a side of the catheter 42 through a fenestration 138 of the endograft 102.

The delivery system 40 can be operated to position the endograft 102 at the implant target site and operated to uncover and expand the constricted endograft 102 from the low-profile configuration to the expanded configuration. The delivery system 40, for example, can also be operated (outside the patient) to partially expose and partially expand the covered endograft 102 within the catheter 42 to provide access to the fenestration 138 to facilitate the introduction of the guidewire 44 into the guidewire path, and operated to constrict and re-cover the exposed portion of the endograft 102 in preparation for the insertion into a patient vasculature. To facilitate these operations, the delivery system 40 provides sliding arrangements between components. For example, the guidewire 42 can be in a sliding arrangement with the components of the delivery system 40 that define the guidewire path. During an implantation procedure, a distal end of the guidewire 44 can be positioned in a patient at a desired location near the target site, and a proximal end of the guidewire 44 may be held by the operator. While the guidewire 44 remains in a static position, the catheter 42 supporting the endograft 102 can be slid over the guidewire 44 in the distal direction 170 with the catheter 42 and endograft 102 passing over the guidewire 44 along the guidewire path. As will be appreciated by those of skill in the art, when the catheter 42 and endograft 102 are slid over the guidewire 44, the bend 44a can appear to move along the guidewire 44 in the distal direction 170 because of the bending and unbending of the guidewire 44 caused by the distal movement of the catheter 42 where the guidewire 44 changes (at the bend 44a) from the transverse direction to the coaxial direction.

To expose at least a portion of the covered endograft 102 (or to re-cover a partially-uncovered endograft 102), the inner tube 62 can be slidably arranged within the pusher tube 76, the nose cone 72 (at the cylindrical wall 74) can be slidably arranged over the distal end of the endograft 102, and the sheath 78 can be slidably arranged over the pusher tube 76 and the proximal end of the endograft 102. For example, with the pusher tube 76 held in a static position, the inner tube 62 can be slid in the distal direction 170 within the lumen of the pusher tube 76 to carry the nose cone 72 forward in the distal direction 170. As the nose cone 72 is moved in the distal direction 170 (based, at least in part, on the movement of the pusher tube 76 supporting the nose cone 72), the cylindrical wall 74 can slide over the distal end of the endograft 102 contained within the delivery chamber 70 to expose the constricted endograft 102. In some embodiments, the endograft 102 can also be exposed by the sliding movement of the sheath 78 in the proximal direction 172 over the proximal end of the endograft 102 and the outer surface of the pusher tube 76.

As will be appreciated by those of skill in the art, the movement of the sheath 78 in the proximal direction 172 and/or the movement of the cylindrical wall 74 in the distal direction 170 can increase the separation 80. Further, the separation 80 may be reduced by the movement of sheath 78 and cylindrical wall 74 towards each other. In some instances, the endograft 102 can slide over the pusher tube 76 in the distal direction 170 due to friction between the self-expanding endograft 102 and the cylindrical wall 74 as the cylindrical wall 74 is moved in the distal direction 170 during the uncovering of the endograft 102. Such movement may be undesirable and interfere with a desired arrangement of the guidewire path and fenestration 138 relative to the implant target site. To inhibit or counter such movement of the endograft 102, in some embodiments the pusher tube 76 may include an abutment 77 that can be held in place or moved in the proximal direction 172 (e.g., by sliding the pusher tube 76 over the inner tube 62) to cause the abutment 77 to contact and maintain the position of the endograft 102 or to nudge the endograft 102 back into a desired position in the proximal direction 172.

Referring again to FIG. 2, in order to maintain the position of the guidewire 44 at a desired location while uncovering the endograft 102, the transverse slot 66 is configured to move past the stationary guidewire 44 within the separation 80, so as to not disturb the position of the guidewire 44. For example, as the inner tube 62 is moved in the distal direction 170, the transverse slot 66 also moves in the distal direction 170 so that the guidewire 44 stays in place (relative to the fenestration 138 and the renal artery (not shown)), resulting in the stationary guidewire 44 starting at one end of the transverse slot 66 and then ending at the opposing end of the transverse slot 66 due to the movement of the inner tube 62. The transverse slot preferably has an axial length of approximately 30 mm and a circumferential width of approximately 1 mm. In some embodiments, the transverse opening 82 of the pusher tube 76 may also comprise a slot (not shown) configured to allow the pusher tube 76 to move in the proximal direction 172 to adjust the position of the endograft 102 relative to the abutment 77. The transverse opening 82 can also be a slot to facilitate the insertion of the guidewire 44 into the guidewire path by providing a larger opening that is sufficiently long and wide to provide access to the underlying transverse slot 66 of the inner tube 62.

When the endograft 102 is carried by the delivery system 40, one end of the endograft 102 can be secured to inner tube 62 and the opposing end of the endograft 102 can be secured to the pusher tube 76. By securing each end of the endograft 102 to the sliding tubes 62 and 76, the ends of the endograft 102 can be moved away from each other to further stretch out the endograft 102 and to reduce the outer diameter of the endograft 102. Likewise, the ends of the endograft 102 can be moved towards each other to reduce the length of the endograft 102 and increase the outer diameter of the endograft 102. Such manipulation of the sliding tubes 62 and 76 can cause selective expansion or constriction of the endograft 102 diameter or cross-sectional dimensions, and can cause selective extension or contraction of the length of the endograft 102. As will be appreciated, manipulation of the sliding tubes 62 and 76 can provide a controlled minimal expansion of the endograft during the insertion of the guidewire 44 through the fenestration 138 and can facilitate positioning of the guidewire 44 in the guidewire path. Further, after satisfactory placement of the guidewire 44 in the guidewire path, the sliding tubes 62 and 76 can be used to stretch the endograft 102 to return the endograft 102 into a covered position suitable for delivery to the implant target site.

Figure 3A:
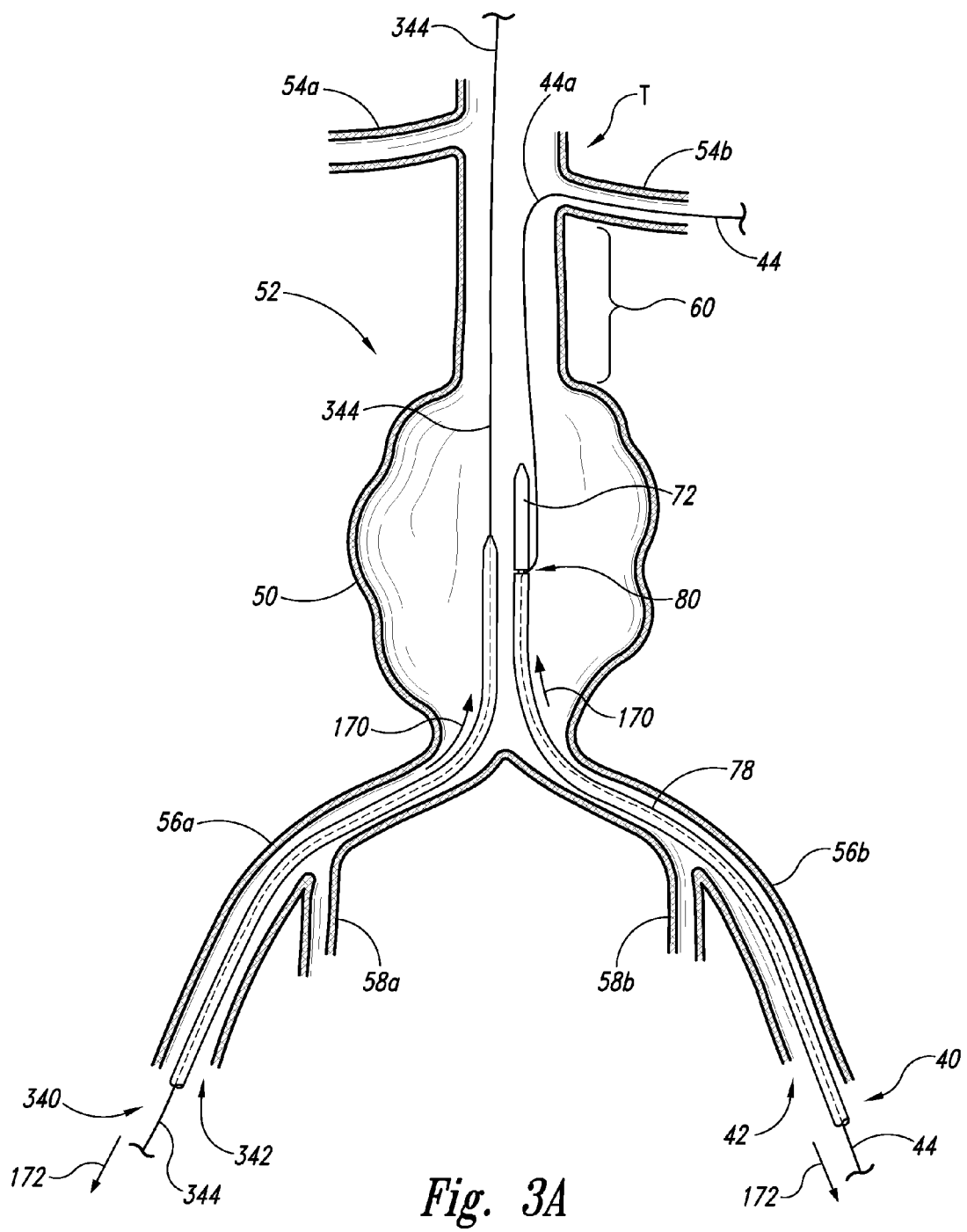
FIGS. 3A-3F are schematic views of a two-part modular endograft system being deployed across an aneurysm in accordance with an embodiment of the technology.

4. Methods of Delivering and Deploying Endograft Systems
   4.1 Delivery and Deployment Described below are methods of delivering and deploying endografts 102 with the endograft delivery system 40 to bypass an aneurysm in accordance with embodiments of the technology are described below. The associated FIGURES (i.e., FIGS. 3A-3F) include schematic representations of an abdominal portion of an aorta. More specifically, FIG. 3A shows an aneurysm 50 located along an infrarenal portion of the aorta 52, which is the most common site of an AAA. A right or first renal artery 54a and a left or second renal artery 54b stem from the aorta 52. The region of the aorta 52 superior to the aneurysm 50 and inferior to the renal arteries 54 is the aortic neck 60. The distal end portion of the aorta 52 bifurcates into common iliac arteries 56 (identified individually as a first iliac artery 56a and a second iliac artery 56b), and the internal iliac arteries 58 (identified individually as a first internal iliac artery 58a and a second internal iliac artery 58b) branch from the common iliac arteries 56. Other arteries and structures proximate to the abdominal portion of the aorta 52 have been removed for clarity.

Figure 3B:
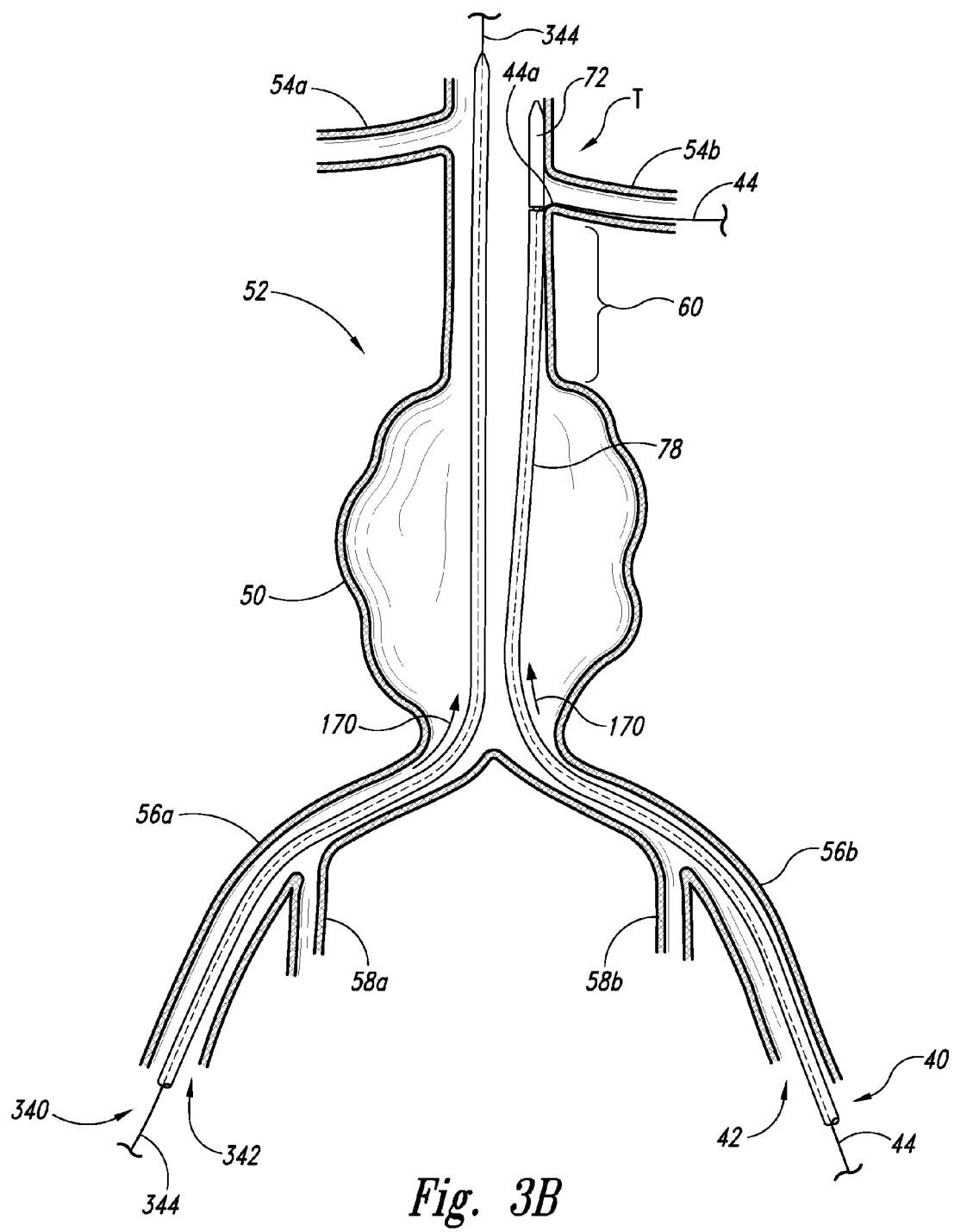

FIGS. 3A and 3B are schematic views of two delivery systems configured in accordance with an embodiment of the technology. More specifically, the delivery system on the right side of the figures is the endograft delivery system 40 described above, and the system on the left of the figures comprises a vascular device delivery system 340 delivering a vascular device 302 (such as the endograft device described in U.S. application Ser. No. 12/958,367, which as noted above is incorporated herein by reference in its entirety) that can be disposed to mate with the endograft 102. The delivery and mating of a vascular device 302 with the endograft 102 embodying one form of the technology is shown in FIGS. 3A and 3B to illustrate a use of the present technology with another device and delivery system. As can be appreciated, any difference between the left and right-side systems does not mean that such difference exists in other embodiments of the present technology. As can be also appreciated, the left-side delivery system 340 shown in FIGS. 3A and 3B can be substituted with the endograft delivery system 40 described above so as to provide for the delivery and mating of two endografts 102 using two endograft delivery systems 40. Furthermore, although FIGS. 3A and 3B show a system on a right side and a system on a left side of the illustrated anatomy, the delivery systems can be disposed to cross each other so that a system introduced from the right-side of the FIGURE can cross over the other system to deliver a device to the left-side of the figure and vice versa. Likewise, the deployed endografts 102 (or endograft 102 and vascular device 302) can be deployed to cross over each other with the use of crossing delivery systems.

Referring to FIG. 3A, endograft delivery system 40 (shown on the right side of FIG. 3A) is configured for delivering and deploying the endograft 102 (not shown because it is enclosed within system 40 in FIG. 3A), and the vascular device delivery system 340 (shown on the left side of FIG. 3A) is configured for delivering and deploying a vascular device 302 (not shown because it is enclosed within system 340 in FIG. 3A). In this embodiment, the endograft delivery system 40 can include a catheter 42 holding an enclosed endograft 102 in the low-profile configuration (not viewable in FIG. 3A) and a guidewire 44 passing through the catheter 42 and the enclosed endograft 102. The vascular device delivery system 340 includes a catheter 342 holding an enclosed vascular device 302 in a constricted configuration (not viewable in FIG. 3A) and a guidewire 344 passing through the catheter 342. Because the endograft 102 is delivered separately from its mating device (i.e., the vascular device 302 or another endograft 102) and is thus one half of a two-part modular endograft system 100, the size of the catheter 42 can be less than a catheter configured to carry a unitary endograft system. In some embodiments, the low-profile configuration of the endograft device 102 can fit within a 12 F or 14 F catheter. In other embodiments, the low-profile configuration of the endograft device 102 can fit within a catheter 42 that has a different size than the catheter associated with the mating device (e.g., the catheter 342 associated with vascular device 302).

In one of the initial steps of the delivery and deployment procedure, the guidewires 44 and 344 can be inserted percutaneously into a blood vessel (e.g., via a femoral artery). With the aid of a suitable imaging system, the distal end of the guidewire 344 can be endoluminally navigated in the distal direction 170 through the vasculature, up the first iliac artery 56a, through the aneurysm 50 and the aortic neck 60, past the first renal artery 54a, and to a location superior to a target site T. Also with the aid of a suitable imaging system, the distal end of the guidewire 44 can be endoluminally navigated in the distal direction 170 through the vasculature, up the second iliac artery 56b, through the aneurysm 50 and the aortic neck 60, into the second renal artery 54b, and to a location beyond the target site T. As shown in FIG. 3A, the guidewire 344 can remain generally straight as it passes through the aortic neck 60 and the target site T. As also shown in FIG. 3A, the guidewire 44 can turn within the aortic neck 60 and/or the target site T as it changes directions to enter the second renal artery 54b, thereby forming an elastic bend 44a in the guidewire 44. It will be appreciated that the bend 44a can be an elastic deformation of the guidewire 44 that remains within the aortic neck 60 and/or the target site T as the guidewire 44 is advanced in the distal direction.

After satisfactory placement of the guidewires 44 and 344, the catheter 42 can then be passed through the vasculature over the guidewire 44 in the distal direction 170 to the target site T (as shown in FIGS. 3A and 3B). As described above with regard to FIG. 2, the guidewire 44 can enter the catheter 42 from the side through the separation 80 where it passes through the fenestration 138 of the enclosed endograft 102 within the catheter 42 and continues on along the guidewire path to the inner lumen 64 of the inner tube 62 to continue in the proximal direction 172. When the catheter 42 is advanced sufficiently to reach the target site T (as shown in FIG. 3B) the distal end of the catheter 42 can slide over the bend 44a in the guidewire 44 and abruptly alter its course from a path following the aortic neck 60 to a path following the second renal artery 54b, which causes the distal end of the catheter 42 to move laterally towards the renal artery 54b. In some instances, this lateral movement of the distal end of the catheter 42 can cause the side of the catheter 42 to engage the arterial wall because the side of the catheter 42 is too large to enter the renal artery 54b in a sideways orientation. The lateral movement of the distal end of the catheter 42 can also press the catheter 42 against the arterial wall and align the fenestration 138 with the end of the renal artery 54b. The catheter 342 can also be advanced over the guidewire 344 until reaching a desired position at the target site. As the catheter 342 slides over the guidewire 344 in a straight path through the aorta 52 that extends beyond the target site T, the catheter 342 is free to advance beyond the target site T unless brought to a proper position while being viewed with an imaging system. In one embodiment, one of the catheters 42 or 342 can be brought into position at the target site T before the other in succession. In other embodiments, however, both catheters 42 or 342 can be brought into position simultaneously or approximately simultaneously.

Figure 3C:
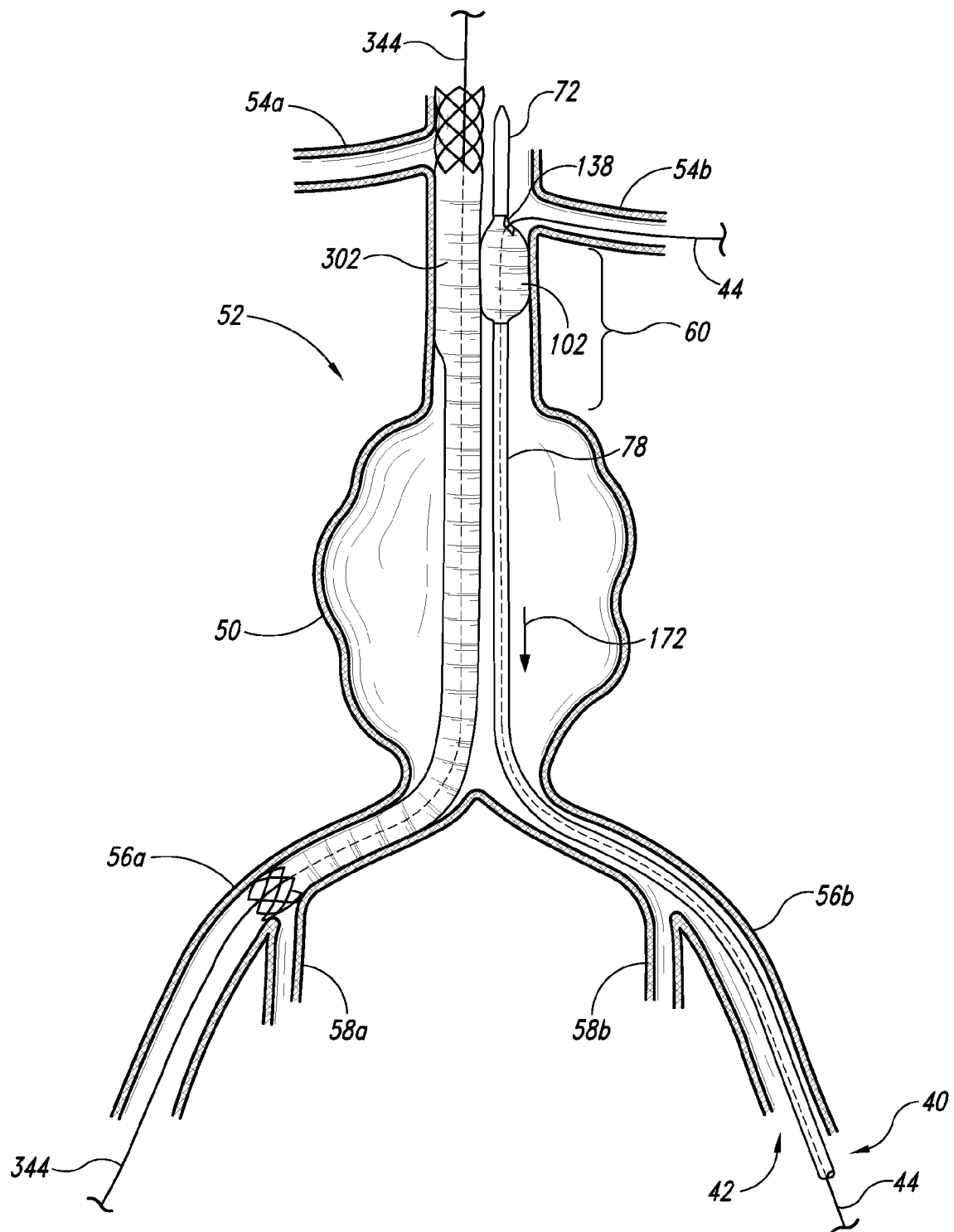

More specifically, the increase of the separation 80 (FIG. 3A) can be achieved by withdrawing the sheath 42 in the proximal direction 172 while holding the endograft device 102 in place due to the transverse passage of the guidewire 44 through the fenestration 138 and/or by using the inner tube 62, pusher tube 76, nose cone 72, or other suitable endovascular instruments to provide an opposing force to the proximal movement of the sheath 78. The increase of the separation 80 may also be achieved by advancing the nose cone 72 away from the sheath 78 and/or fenestration 138, with the position of the endograft 102 being maintained due to the transverse passage of the guidewire 44 through the fenestration 138 and/or with the sheath 78 or the abutment 77 of the pusher tube 76 providing an opposing force to the movement of the nose cone 72. In some embodiments, the increase of the separation 80 may also be achieved by simultaneous movement of the nose cone 72 and sheath 78 away from each other with the position of the endograft 102 maintained by the transverse passage of the guidewire 44 through the fenestration 138 and/or with controlled movements of the nose cone 72 and sheath 78 that keep one component from dominating the uncovering of the endograft 102. As shown in FIG. 3C, the vascular device 302 can be uncovered using suitable means appropriate for the design of the catheter 342, and the catheter 342 may be ultimately removed from the vasculature (for clarity the catheter 342 has been removed from the vascular device shown in FIG. 3C but, as will be appreciated, the catheter 342 could remain over a portion of the vascular device 302 in a partial deployment of vascular device 302). In an embodiment where two endografts 102 are implanted, the deployment process can be essentially the same for both endografts 102. In still other embodiments, other suitable deployment arrangements may be used.

In some embodiments, during uncovering of the endograft 102, the first portion of the endograft 102 to be uncovered can be near the separation 80. This partial uncovering of the endograft 102 can allow a partial expansion of the endograft 102 as shown in FIG. 3C, which is a point in the deployment when the endograft 102 can be moved slightly into a better position or rotated. This positioning or rotating can be done to improve the position of the endograft 102 relative to local anatomical features, to better position the endograft 102 relative to the mating device (the vascular implant 302 or second endograft 102), to achieve better mating between the septal wall 114 of the endograft 102 and the opposing wall of the mating device (the vascular implant 302 or second endograft 102), to improve seating of anchors extending from the endograft 102, and/or to improve alignment of the fenestration 138 of the endograft 102 with the second renal artery 54b. The endograft 102, the sheath 78, and the nose cone 72 can also be configured to allow the re-covering of the partially expanded endograft 102 by decreasing the separation 80 to cause the endograft 102 to return fully to the low-profile configuration or to return to a more constricted configuration suitable for repositioning of the endograft 102 or for removal of the endograft 102 from the vasculature if removal is warranted.

Figure 3D:
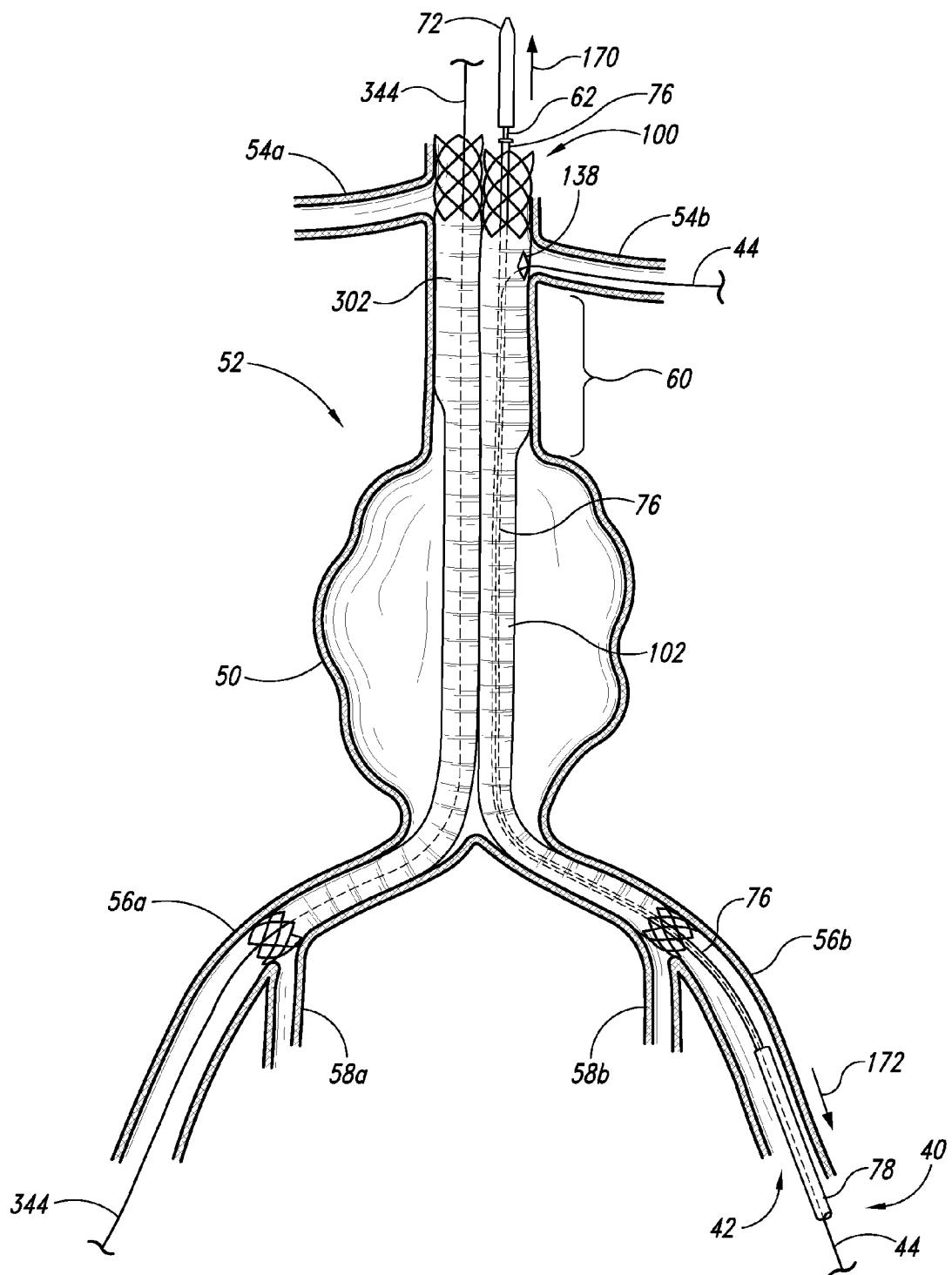

Referring to FIG. 3D, a fully-deployed vascular device 302 is seated next to the endograft 102 to provide an implanted modular endograft system 100. In the illustrated embodiment, proximal movement of the sheath 78 (in the proximal direction 172) and distal movement of the nose cone 72 (in the distal direction 170) bring the endograft 102 from the partially uncovered and partially expanded configuration shown in FIG. 3C to the fully uncovered and fully expanded configuration shown in FIG. 3D. Referring to FIG. 3D, the nose cone 72 (mounted on the distal end of the inner tube 62 and in part within the pusher tube 76) has advanced sufficiently in the distal direction 170 to allow the distal end of the endograft 102 to expand to a diameter greater than the cylindrical wall 74 of the nose cone 72. Further, the sheath 78 has withdrawn sufficiently in the proximal direction 172 to allow the proximal end of the endograft 102 to expand. As shown in FIG. 3D, the sheath 78 can be withdrawn (in the proximal direction 172) from the target site T and the endograft 102 to leave the inner tube 62 and the pusher tube 76 in place within the lumen 116 of the endograft 102 to support the nose cone 72 as it extends distal to the endograft 102. The guidewire 44 can continue to pass through the fenestration 138 of the expanded endograft 102, and continue through the transverse opening 82 and the transverse slot 66 and into the inner lumen 64 in the proximal direction 172.

Figure 3E:
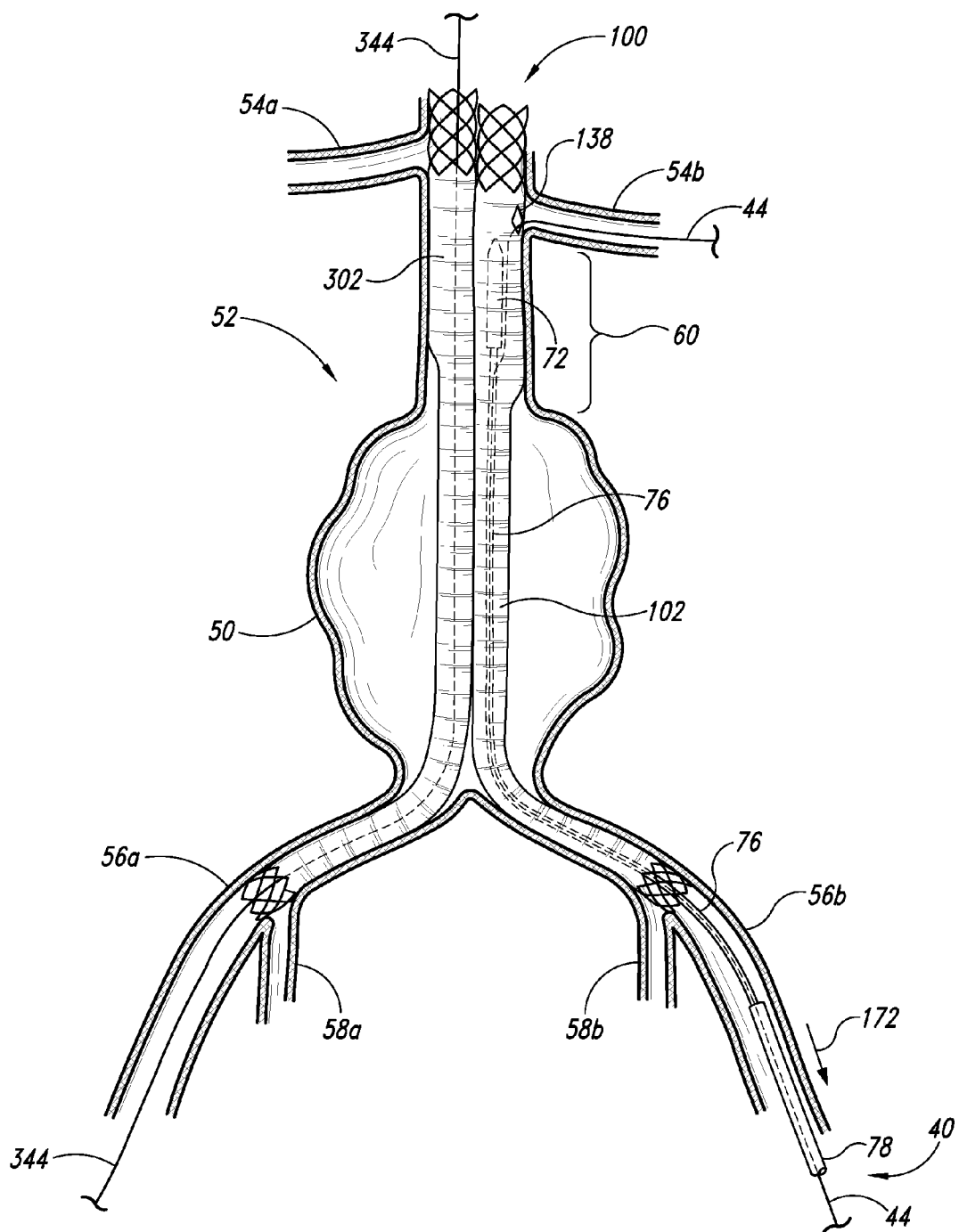

FIG. 3E illustrates withdrawal of the pusher tube 76, inner tube 62, and nose cone 72 in the proximal direction 172 from the endograft 102. The nose cone 72, which has an outer diameter that is less than the inner dimensions of the lumen 116 of the endograft 102, can be withdrawn in the proximal direction 172 as it slides over the guidewire 44. The pusher tube 76, inner tube 62, and nose cone 72 along with the sheath 78 (unless removed already) can then be removed from the patient entirely and dismounted from the guidewire 44 at the proximal end of the guidewire 44. After the removal of the pusher tube 76, inner tube 62, nose cone 72, and sheath 78, the remaining components in the patient can be the two guidewires 44 and 344 (unless guidewire 344 has already been removed), the endograft 102, and the vascular device 302.

Figure 3F:
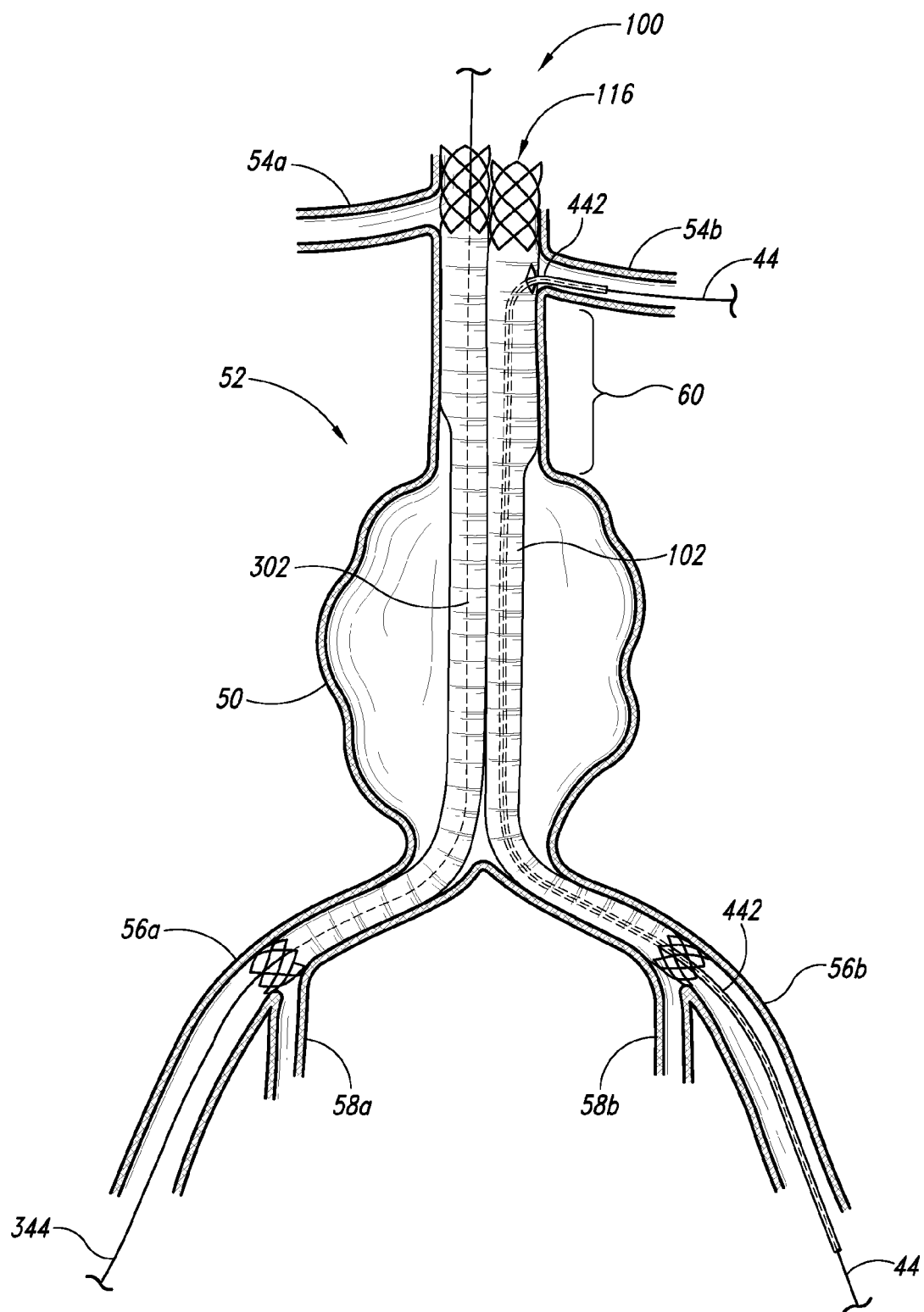

FIG. 3F illustrates introduction of a stent catheter 442 over the guidewire 44 carrying a stent (not shown) in a constricted configuration within the stent catheter 422. The stent and the stent catheter 442 can be sized and configured to advance through the lumen 116 of the endograft 102, navigate the bend 44a, and pass through the fenestration 138 and enter the second renal artery 54b. The stent can also be sized and configured to approach the endograft 102 and engage the fenestration 138 from the distal end of the guidewire 44. In one embodiment, the stent can be a self-expanding stent that expands when a covering sheath is retracted, and can have surface features that facilitate the engagement of the stent to the endograft 102 at the fenestration 138. The stent can also have end portions that flare outward within the lumen 116 to engage the endograft 102 with the remainder of the stent extending away from the endograft within the second renal artery 54b. The stent can also include surfaces, surface features, a covering graft, or other coatings or coverings that enhance the sealing of the stent with the walls of the second renal artery 54b and to inhibit blood flow around the outside of the stent. In other embodiments, the stent may have a different arrangement and/or different features.

After the stent has been expanded within the second renal artery 54b, the stent catheter 442 can be removed from the patient, and the guidewires 44 and 344 can also be removed. As can be appreciated, the sequence of the steps in the above-described methods and the introduction, use, and withdrawal of components can be modified to achieve the delivery and deployment of the endograft 102 and/or the stent engaging the fenestration 138 of the endograft 102.

4.2 Endograft System Sealing and Alignment

Referring back to FIGS. 1A and 1B, the endograft device 102 (with or without a fenestration 138) can be positioned at its desired location independently of the mating device while the endograft device 102 is in, or at least partially within, the catheter 42 (FIG. 2). The independent positioning feature can allow for an offset of one device relative to the other such that an end of one device can extend farther than the other in the proximal or distal direction. Further, even with this offset, the inherent hoop force of the mating frames 104 caused by the constant outward spring force of the wire 126 braid at least substantially seals (a) the covers 106 at the outer walls 112 against the aortic neck 60 and (b) the septal walls 114 to each other to form the septum 120.

When additional sealing is desired, extension units (not shown) can be added to the system 100 after the first and second endografts 102 are positioned within the aortic neck 60. Example extension units are shown and described in U.S. application Ser. No. 12/958,367, which as provided above is incorporated herein by reference in its entirety. The endograft system 100 can include extension units projecting distally from the superior termini 131 of the covers 106. The extension units can include an extension frame and an extension cover at least generally similar to the frame 104 and the cover 106 of the endograft devices 102 described above. The extension units can have a substantially similar shape as the superior portions 108 of the endograft devices (e.g., a D-like shape) such that the extension units can mate with the interior of at least a part of the superior portions 108. For example, the extension covers can be positioned inferior to the renal arteries 54 within the frame 104 such that the extension covers can interface with the aortic neck 60 and mate with one another to extend the septum 120 distally. Therefore, the extension units can increase the fixation area and the sealing area of the endograft devices 102 when the superior termini 131 of the covers 106 of the endograft devices 102 are offset from the entrances of the renal arteries 54 or where additional length or support is needed. For example, in some embodiments, the extension units add approximately one inch of fixation structure and sealing area to the endograft devices 102. In other embodiments, the inferior portions 110 can also include extension units that can affix and at least substantially seal to the iliac arteries 56.

The extension units can be deployed from catheters at desired positions within the first and second frames 104. Upon deployment, the extension units can self-expand via an inherent spring force in the extension frame to an expanded configuration to contact and at least substantially seal with the interior of the superior portions 108 of the endograft devices 102. The extension cover can interface with the first end portions 118a of the frames 104 to strengthen the seal therebetween. In other embodiments, the extension units can connect and seal to the endograft devices 102 using other suitable attachment methods. Similarly, the inferior portions 110 can include extension units that increase the sealing area with the iliac arteries 56.

The embodiments of the present technology, such as shown in FIG. 1B, can have superior portions 108 that are longitudinally offset from each other. For example, in some embodiments, the superior portions 108 are longitudinally offset by at least 5 mm. One or both of the superior portions 108 can be placed superior to the transverse arteries to increase the available fixation structure and sealing area for the endograft devices 102 without inhibiting blood flow through the fenestrations 138. In such offsetting, the interplay between the woven wires 126 of the frame 104 of the first endograft device 102a restricts the outward movement of the first end portion 118a of the first endograft device 102a and provides substantially continuous support along the length of the frame 104 such the free first end portion 118a retains substantially the same shape as if it were supported. When the endografts 102 are offset, these features maintain the generally straight or convex shape of the unsupported septal region of the first portion 118a of the first endograft device 102a. Using shape-setting Nitinol wire in the frame 104 can further facilitate maintaining the shape of the unsupported portion of the frame 104.

Independent positioning or staggering of the endograft devices 102 can also include positioning the devices independently such that the fenestration 138 of the each endograft device 102 is aligned with a corresponding left or right renal artery. By providing an opening through the cover 106 that can communicate with the renal artery, the frame 104 extending past the termini 131 of the cover 106 can be dedicated to providing a sealing area between the outer walls 112 and the arterial walls. Also, by providing an opening through the cover 106 that can communicate with a renal artery, the frame 104 extending past the termini 131 of the cover 106 can facilitate the independent positioning of the superior portions 108 over the renal arteries such that one endograft device 102 (of a mating pair) does not need to be limited to the elevation of the inferior renal artery. This increase in the available sealing area and the ability to provide a sealing area unconstrained by the location of the renal artery facilitates optimal placement for each endograft device 102 within the vasculature without requiring devices with customized superior portions 108. This feature is expected to allow offsetting or staggering without degradation of such sealing or support. Endograft devices 102 that are staggered can take advantage of such additional endograft end structure for fixing the endograft devices 102 to arterial walls and increasing the available sealing area in the aortic neck 60. The longer fixation and sealing areas along the outer wall 112 of the endograft devices 102 and the longer mating and sealing areas between the septal walls 114 can strengthen the seals of the system 100 as a whole to reduce the likelihood of endoleaks. Additionally, the system 100 can be offset or staggered to accommodate an anatomy with less fixation and sealing area in one of the iliac arteries 56. In other embodiments, the endograft devices 102 may include one or more additional fenestrations 138 to increase the available sealing area without restricting blood flow. For example, the inferior portions 110 can include one or more fenestrations 138 that allow the inferior portions 110 to extend over the entrance of the internal iliac arteries.

In some embodiments, alignment aids, such as the alignment aids described above, are used to rotationally orient the endograft devices 102 and align the septal walls 114 during delivery. Additionally, to prevent migration and/or projection of the system while in situ, anchors, such as the anchors described above, can be deployed from the outer walls 112 to engage the arterial walls of the aortic neck 60 and/or from the second end portions 118b to engage the arterial walls of the iliac arteries 56. Example alignment aids and anchors are shown and described in U.S. application Ser. No. 12/958,367, incorporated herein by reference.

In the embodiment illustrated in FIGS. 3A-3F, the aneurysm 50 is shown in the infrarenal portion of the aorta 52, a common site of an AAA. In other embodiments, however, the modular endograft system 100 may be deployed across aneurysms 50 at different portions of the aorta 52 or in other vessels altogether. In some embodiments, for example, the aneurysm 50 can extend from the infrarenal portion of the aorta 52 into one or both of the common iliac arteries 56. The inferior portions 110 of the systems 100 can extend past the diseased, aneurysmal portion of the iliac arteries 56 without blocking blood flow to the internal iliac arteries 58. In still other embodiments, the system 100 can be deployed across aneurysms 50 located in the supra renal portion of the aorta 52 with the fenestrations 138 and/or a stent positioned at the entrance of the renal arteries 54. In still further embodiments, the systems described herein may be deployed across aneurysms in other portions of the vasculature that benefit from the use of a bifurcated, bi-luminal modular endograft system that can be independently positioned.

CONCLUSION

From the foregoing, it will be appreciated that specific embodiments of the technology have been described herein for purposes of illustration, but that various modifications may be made without deviating from the spirit and scope of the technology. For example, the embodiments illustrated in FIGS. 1A-3F include covers 106 that extend over the exterior of the integrated frames 104. However, other embodiments of the technology can include covers 106 that are attached to the interior of the integrated frame 104 and/or are formed integrally with the frame 104. Further, in some embodiments a removable guidewire insertion aid (e.g., a liner, a shoehorn) can be provided to facilitate the introduction of the guidewire 44 through the separation 80, through the fenestration 138, and into the guidewire path, with the guidewire insertion aid oriented to direct the guidewire into the transverse opening 82 of the pusher tube 76 and into the transverse slot 66 of the inner tube 62 so that the guidewire 44 can enter the inner lumen 64.

Certain aspects of the new technology described in the context of particular embodiments may be combined or eliminated in other embodiments. For example, in the embodiments illustrated above, each endograft device 102 includes a singular lumen 116. However, the endograft devices can include additional lumens that transverse, bisect, and/or otherwise communicate with the lumen 116 to accommodate the vasculature. For example, the endograft devices can include lumens that extend into the renal arteries, the internal iliac arteries, and/or other arteries. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:
1. An endograft delivery system, comprising:
a catheter defining a catheter axis and opposing proximal and distal ends, the proximal and distal ends of the catheter defining a proximal direction and a distal direction along the catheter axis, wherein the distal end of the catheter comprises—
an inner tube having a distal end and an inner lumen extending within the inner tube, the distal end of the inner tube having a transverse slot communicating with the inner lumen, the transverse slot extending in the proximal direction;
a nose cone engaging the distal end of the inner tube, the nose cone having a cylindrical wall extending in the proximal direction to a cylindrical wall edge to cover at least a portion of the distal end of the inner tube and define a first internal volume within the cylindrical wall of the nose cone;
a pusher tube slidably disposed over the inner tube, the pusher tube having a distal end at least in part disposed within the first internal volume of the nose cone, the distal end of the pusher tube having a transverse opening communicating with the inner tube; and
a sheath slidably disposed over the pusher tube and having a distal end terminating at a sheath edge disposed to face the cylindrical wall edge of the nose cone to define a separation therebetween, the distal end of the sheath and the pusher tube defining a second internal volume therebetween that communicates with the first internal volume to define a delivery chamber; and
an endograft device disposed within the delivery chamber of the catheter, the endograft device comprising an expandable frame in a low-profile configuration within the delivery chamber and configured to expand to an expanded configuration when the separation between the sheath edge and the cylindrical wall edge is sufficiently increased to uncover the endograft device,
wherein the catheter and the endograft together define a guidewire path configured to direct a guidewire through the endograft delivery system, wherein the guidewire path comprises a proximal end extending in the proximal direction within the inner lumen of the inner tube and a distal end extending through the separation between the sheath edge and the cylindrical wall edge of the nose cone, the guidewire path further passing through the transverse slot of the inner tube and the transverse opening of the pusher tube proximate to the separation.

2. The endograft delivery system of claim 1 wherein:
the endograft device further comprises a cover attached to the frame, the cover having a superior terminus and an inferior terminus, the frame having a first end extending distally beyond the superior terminus of the cover and a second end extending proximally beyond the inferior terminus of the cover,
wherein the superior terminus of the cover and the first end of the frame define a superior portion of the endograft and a lumen of the endograft, the superior portion having a fenestration passing through the cover and the frame to communicate with the lumen.

3. The endograft delivery system of claim 2 wherein at least a portion of the fenestration is disposed at a distance up to approximately 5 mm from the superior terminus of the cover.

4. The endograft delivery system of claim 2 wherein the fenestration passing through the cover comprises a slot extending towards the superior terminus of the cover.

5. The endograft delivery system of claim 2 wherein the fenestration is configured to engage a stent.

6. The endograft delivery system of claim 1 wherein the transverse slot of the inner tube has an axial length of approximately 30 mm and a circumferential width of approximately 1 mm.

7. The endograft delivery system of claim 1 wherein the transverse opening of the pusher tube is a slot extending in the proximal direction.

8. The endograft delivery system of claim 1 wherein the distal end of the pusher tube has an abutment configured to limit movement of the endograft when the inner tube and the nose cone are moved together in the distal direction.

9. The endograft delivery system of claim 1 wherein the guidewire path is configured to remain in place adjacent an implant target site when the sheath is moved in the proximal direction and the inner tube and the nose cone are moved together in the distal direction.

10. The endograft delivery system of claim 1 wherein the frame of the endograft has a superior portion and an inferior portion, and wherein the superior portion has an outer wall configured to engage a wall of a blood vessel and a septal wall configured to press against a vascular device.

11. The endograft delivery system of claim 10 wherein the outer wall and the septal wall, respectively, define first and second complex ellipsoids in the expanded configuration with the outer wall having a first radius and the septal wall having a second radius greater than the first radius, and wherein, in the expanded configuration, the first and second complex ellipsoids comprising a substantially D-shaped cross-section.

12. The endograft delivery system of claim 11 wherein the endograft outer wall and septal wall define a lumen of the endograft, the outer wall having a fenestration passing through the outer wall and communicating with the lumen, the fenestration defining an angle relative to the septal wall corresponding to an angulation of a renal blood vessel observed at an implant target site.

13. The endograft delivery system of claim 1 wherein the endograft further comprises a cover, the cover having a superior terminus and an inferior terminus, the cover attached over the frame at the superior terminus and the inferior terminus of the cover, the cover and the frame configured such that the cover substantially conforms to the frame in the expanded configuration.

* * * * *